United States Patent
Cao

(10) Patent No.: US 10,603,325 B2
(45) Date of Patent: Mar. 31, 2020

(54) METHODS OF TREATING AGE-RELATED SYMPTOMS IN MAMMALS AND COMPOSITIONS THEREFOR

(71) Applicant: University of Maryland, College Park, MD (US)

(72) Inventor: Kan Cao, Bowie, MD (US)

(73) Assignee: UNIVERSITY OF MARYLAND, College Park, MD (US)

(*) Notice: Subject to any disclaimer, the term of this patent is extended or adjusted under 35 U.S.C. 154(b) by 0 days.

(21) Appl. No.: 15/521,804

(22) PCT Filed: Oct. 27, 2015

(86) PCT No.: PCT/US2015/057510
§ 371 (c)(1),
(2) Date: Apr. 25, 2017

(87) PCT Pub. No.: WO2016/069556
PCT Pub. Date: May 6, 2016

(65) Prior Publication Data
US 2017/0246177 A1    Aug. 31, 2017

Related U.S. Application Data

(60) Provisional application No. 62/069,890, filed on Oct. 29, 2014.

(51) Int. Cl.
| | | |
|---|---|---|
| *A61K 31/5415* | (2006.01) | |
| *A61Q 19/08* | (2006.01) | |
| *A61K 8/42* | (2006.01) | |
| *A61K 9/00* | (2006.01) | |
| *A61K 8/49* | (2006.01) | |
| *A61K 31/436* | (2006.01) | |
| *A61K 9/10* | (2006.01) | |
| *A61P 17/00* | (2006.01) | |
| *A61K 8/06* | (2006.01) | |
| *A61K 9/107* | (2006.01) | |
| *A61Q 19/00* | (2006.01) | |
| *A61Q 19/10* | (2006.01) | |

(52) U.S. Cl.
CPC .......... *A61K 31/5415* (2013.01); *A61K 8/06* (2013.01); *A61K 8/49* (2013.01); *A61K 8/4926* (2013.01); *A61K 9/0014* (2013.01); *A61K 9/0053* (2013.01); *A61K 9/10* (2013.01); *A61K 9/107* (2013.01); *A61K 31/436* (2013.01); *A61P 17/00* (2018.01); *A61Q 19/00* (2013.01); *A61Q 19/08* (2013.01); *A61Q 19/10* (2013.01); *A61K 2800/92* (2013.01)

(58) Field of Classification Search
CPC ...... A61K 31/5415; A61K 8/042; A61K 8/49; A61K 9/0014; A61Q 19/08
See application file for complete search history.

(56) References Cited

U.S. PATENT DOCUMENTS

| | | | |
|---|---|---|---|
| 5,152,991 A | 10/1992 | Vogel et al. | |
| 6,346,519 B1* | 2/2002 | Petrus | A61K 31/7004 514/61 |
| 2002/0091424 A1* | 7/2002 | Biel | A61K 31/54 607/88 |
| 2002/0141959 A1* | 10/2002 | Peterson | A01N 55/00 424/70.12 |
| 2003/0044406 A1* | 3/2003 | Dingivan | A61K 39/39541 424/130.1 |
| 2006/0223729 A1* | 10/2006 | Hamblin | A61K 41/0019 510/130 |
| 2010/0256576 A1* | 10/2010 | Aggarwal | A61K 31/235 604/265 |
| 2010/0260733 A1 | 10/2010 | Qi | |
| 2013/0281408 A1 | 10/2013 | Levy | |
| 2014/0038963 A1 | 2/2014 | Hect | |
| 2014/0274964 A1 | 9/2014 | Gordon et al. | |

OTHER PUBLICATIONS

Valcarcel-Ares et al. "Mitochondrial dysfunction promotes and aggravates the inflammatory response in normal human synoviocytes" Rheumatology, 2014, vol. 53, pp. 1332-1342. (Year: 2012).*

* cited by examiner

*Primary Examiner* — Samira J Jean-Louis
(74) *Attorney, Agent, or Firm* — Juneau & Mitchell; William E. Beaumont

(57) ABSTRACT

A method of alleviating age-related symptoms in a mammal, which comprises a step of administering to a mammal in need thereof, an effective amount of a composition containing an effective amount of at least methylene blue.

13 Claims, 23 Drawing Sheets

THE 3D skin tissue: EPI-200 skin issue

HISTOLOGY OF EPIDERMFT

H&E Stained paraffin section reveals epidermis containing basal, spinous, granular keratinocytes and stratum corneum. Dermis contains numerous viable fibroblasts (400X).

ECM Gene Expression analysis

| Genes | MB 0.1μM | MB 0.5μM | MB 2.5μM |
|---|---|---|---|
| AC002094.1 | | Up | up |
| COL2A1 | | Up | Up |
| IGF1 | | Up | Up |
| KLK3 | | Up | Up |
| Elastin | Down | Up | Up |
| MMP9 | Down | Down | Down |
| LAMC2 | Down | Down | Down |

FIG. 14

METHODS OF TREATING AGE-RELATED SYMPTOMS IN MAMMALS AND COMPOSITIONS THEREFOR

CROSS-REFERENCE TO RELATED APPLICATION

This PCT application claims priority to U.S. provisional application 62/069,890, filed on Oct. 29, 2014.

STATEMENT REGARDING FEDERALLY-SPONSORED RESEARCH OR DEVELOPMENT

This invention was funded by government support under R00AG029761 by the National Institutes of Health (NIH), and NIH/NHGRI grant R21AG043801. The government has certain rights in the invention.

BACKGROUND OF THE INVENTION

HGPS and Normal Aging

Hutchinson-Gilford progeria syndrome (HGPS) is a rare, autosomal dominant disorder characterized by rapid, premature aging in children. Typically, affected children succumb to cardiovascular diseases, like heart attack or stroke, in their early teens. In addition to the severe cardiovascular diseases, HGPS patients experience problems with many other organ systems including the skin, fat and bone.

HGPS is caused by a C to T mutation in the $11^{th}$ exon of the lamin A gene (LMNA) which leaves the protein code unchanged, instead activating a cryptic splice site. When used, this splice site removes the last 150 nucleotides from the $11^{th}$ exon, resulting in an internal 50 amino acid deletion in the lamin A protein. This deletion interferes with post-translational processing by removing a key protease cleavage site, leading to permanent farnesylation and aberrant anchorage of the mutant lamin A, termed progerin, to the nuclear membrane. The abnormal presence of progerin disrupts the integrity of the nucleoskeleton, causing high levels of nuclear abnormalities, including nuclear blebbing, altered chromatin organization, transcriptional changes and aberrant mitosis.

Mitochondria are complex organelles that are believed to play a significant role in biological aging. They form a sophisticated, dynamic, tubular network that moves along microtubules and actin fibers. Mitochondria undergo a delicate balance between fusion and fission to maintain a functional population, where dysfunctional mitochondria are removed via autophagy and destroyed while new mitochondria are created to replace them. Dysfunctional mitochondria can cause systemic problems, increasing amounts of reactive oxygen species (ROS), and triggering DNA and protein damage.

Due to their ability to induce cellular distress as they accrue damage, mitochondria are believed to play a role in biological aging. PGC-1α, a transcription factor and key regulator of mitochondrial biogenesis has been found to be dramatically down-regulated by nearly 40 folds in HGPS iPSC-derived adipocytes compared to control adipocytes. HGPS patient cells have also been shown to exhibit increased ROS levels in multiple tissues. In addition, a marked downregulation of mitochondrial oxidative phosphorylation proteins and a reduced ATP have been reported in HGPS fibroblasts as well as in progeria mouse models. These evidences suggest that the mitochondria in HGPS cells might be dysfunctional.

It is known that the proper mitochondrial functions are guaranteed by their structural integrity. However, to date, the information on the structure and behavior of mitochondria in HGPS cells remains incomplete. More importantly, it remains unclear that, to what extent, the mitochondrial dysfunction contributes to the premature aging phenotypes in HGPS cells. Clearly, there is a need to better characterize the contribution of mitochondrial dysfunction to both aging, and even premature aging (progeria), and to provide a method for treating this dysfunction, and, consequently, age-related conditions generally.

Further, it is now known that the effects of the improperly processed version of the lamin A protein, called progerin, that accumulates in HGPS cells and wreaks havoc on cellular form and function, may be mitigated by rapamycin and analogues thereof. Moreover, several studies have shown that normal human cells also express tiny amounts of progerin, which accumulates as a person ages, and that rapamycin is effective in degrading and clearing progerin by stimulating autophagy as well as slowing senescence and reducing or abolishing a reduced integrity of the nuclear scaffold, i.e., nuclear blebbing.

Thus, a need exists for a method for alleviating the symptoms of both HGPS and normal aging, including inducing clearance of progerin from aging cells.

A need also exists for a compound or composition for alleviating the symptoms of both HGPS and normal aging, including clearance of progerin from aging cells.

Further, a need exists for a method and compound or composition for alleviating the symptoms of both HGPS-aging and normal aging in mammalian skin, particularly human skin.

BRIEF SUMMARY OF THE INVENTION

The present inventor has investigated the morphological and functional defects of mitochondria in HGPS. As a result of these investigations, it has been discovered that antioxidants as described herein which are particularly targeted to mitochondria, may be advantageously used to alleviate premature aging associated with mitochondria in mammals, and, in particular, in humans.

Accordingly, the present invention provides a method for alleviating premature aging in a mammal, which entails administering a topical pharmaceutical composition containing one or more mitochondria-targeted antioxidant compounds which target mitochondria in the mammal to the mammal.

Further, the present invention provides a topical pharmaceutical composition containing one or more mitochondria-targeted antioxidant compounds which target mitochondria in mammals, and, in particular, in humans, in an excipient.

Moreover, the present invention also provides a method for alleviating premature aging in a mammal, including decreasing formation of insoluble protein aggregates and inducing clearance of the protein aggregates by autophagy in normal fibroblasts, which entails administering a topical pharmaceutical composition containing rapamycin and/or an analogue thereof, and or more mitochondria-targeted antioxidants to the mammal.

Further, the present invention also provides a topical pharmaceutical composition containing rapamycin and/or an analogue thereof, and one or more mitochondria-targeted antioxidants in an excipient.

BRIEF DESCRIPTION OF THE DRAWINGS

All Scale bars in the figures below are 20 µM.

Sol %=Sol/(Sol+Insol)×100%; Insol= Insol/(Sol+Insol)×100%.

(H) Pie graphs showing the combined analyses of soluble and insoluble fractions of lamin A and lamin C (A+C) in normal cells.

(I) Percentages of soluble (Green) and insoluble (Orange) fractions of lamin A (including prelamin A), progerin and lamin C in HGPS cells. Data for each protein were collected based on the band intensities.

Sol %=Sol/(Sol+Insol)×100%; Insol %=Insol/(Sol+Insol)×100%

(J) Pie charts showing the combined analyses of soluble and insoluble fractions of lamin A, progerin and lamin C (A+P+C) in HGPS cells.

FIG. 5(A)-(G): Methylene Blue Improves Mitochondrial Function and Rescues Heterochromatin Loss Pheotype in HGPS Cells
  (A) ATP production in normal and HGPS fibroblasts treated with vehicle or MB 100 nM for 5 weeks (**$p<0.01$).
  (B) Relative fold change of mitochondrial superoxide levels (MitoSOX, Left) and intracellular ROS levels (DCFDA, Right) measured by FACS analysis in normal and HGPS fibroblasts that were treated with vehicle or MB 100 nM for 8 weeks (*$p<0.05$; **$p<0.01$).
  (C) Percentages of mitochondria with different levels of abnormalities in normal and HGPS fibroblasts that were treated with vehicle or MB 100 nM for 8 weeks. The total number of mitochondria that were blindly scored in each group is indicated in the parentheses (*$p<0.05$; ***$p<0.001$ by Chi-square test).
  (D) Upper: Western blot analysis with anti-PGC-1α and anti-β-actin anti-bodies in normal and HGPS fibroblasts treated with vehicle or MB 100 nM for 8 weeks. Lower: Quantitative RT-PCR analysis of PGC-1α expression in normal and HGPS fibroblasts treated with vehicle or MB 100 nM for 8 weeks (*$p<0.05$; **$p<0.01$).
  (E) Representative TEM graphs showing ultrastructure of the nuclear morphology at 3.15 k magnification (Upper panel) and heterochromatin distribution along the nuclear envelope at 40 k magnification (Lower panel) in HGPS fibroblasts treated with vehicle or MB for 8 weeks.
  (F) Representative immunofluorescence images of normal and HGPS fibroblasts treated with vehicle or MB 100 nM for 6 weeks. Green: anti-HP1α antibody, Red; anti-lamin A/C antibody.
  (G) Western blotting analyses with anti-HP1α or anti-β-actin antibodies in normal and two HGPS fibroblasts treated with vehicle or MB 100 nM for 6 weeks. (Upper panel). Normalized relative HP1α protein levels in each sample are shown in the lower graph.

Figure 6:
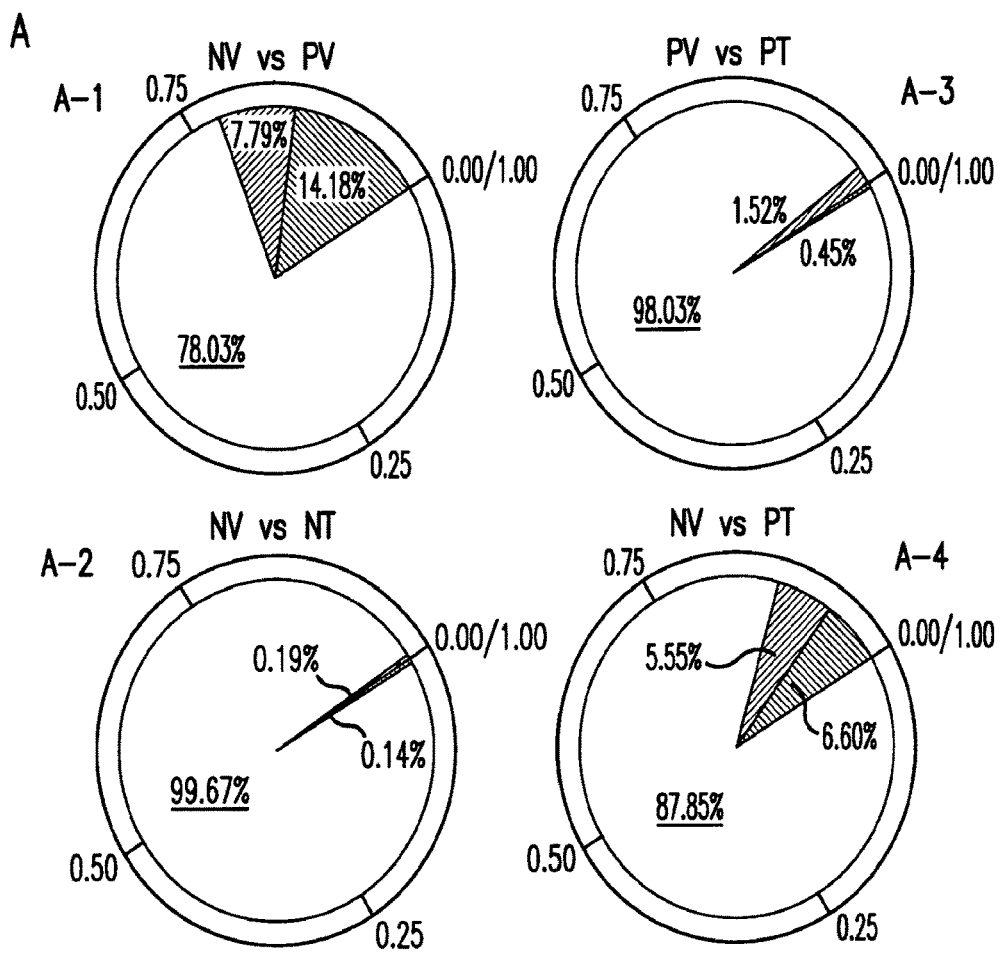

FIG. 6(A)-(B): Methylene Blue Rescues Gene Expression in HGPS Cells
  (A) Pie chart showing the percentages and (B) the counted gene numbers of unaffected- and affected-genes in paired comparison among four groups (Normal+Vehicle vs. Progeria+Vehicle; Normal+Vehicle vs. Normal+MB; Progeria+Vehicle vs. Progeria+MB; and Normal+Vehicle+Progeria+MB).

Figure 7:
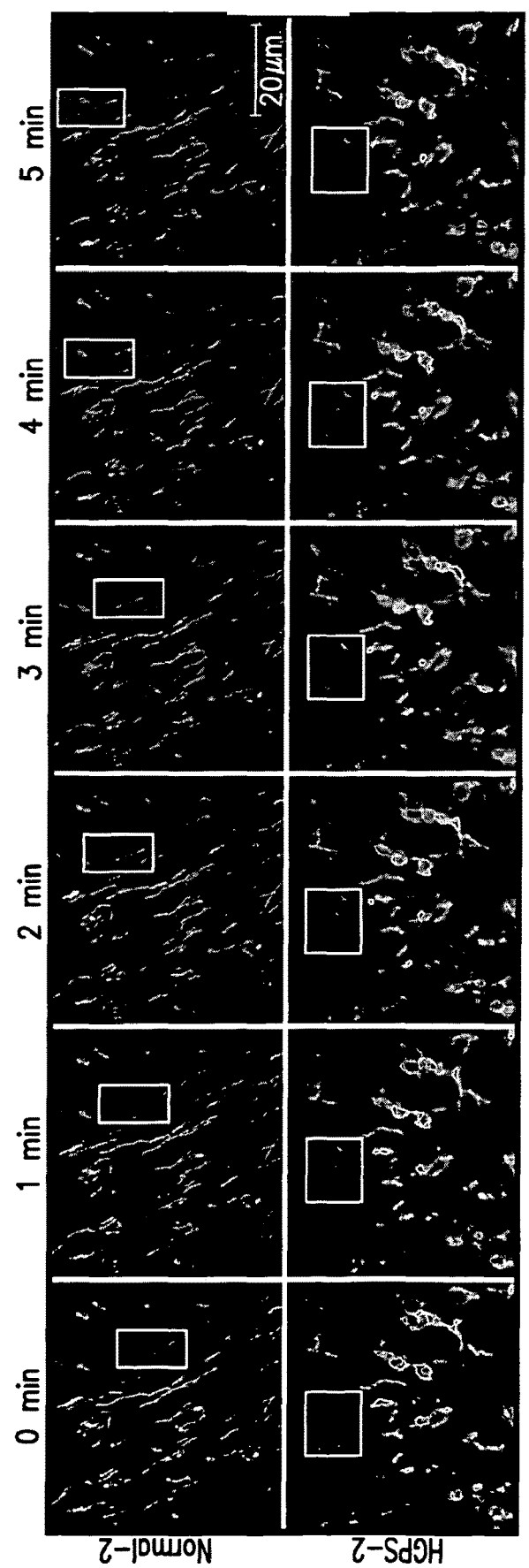
Figure 7:
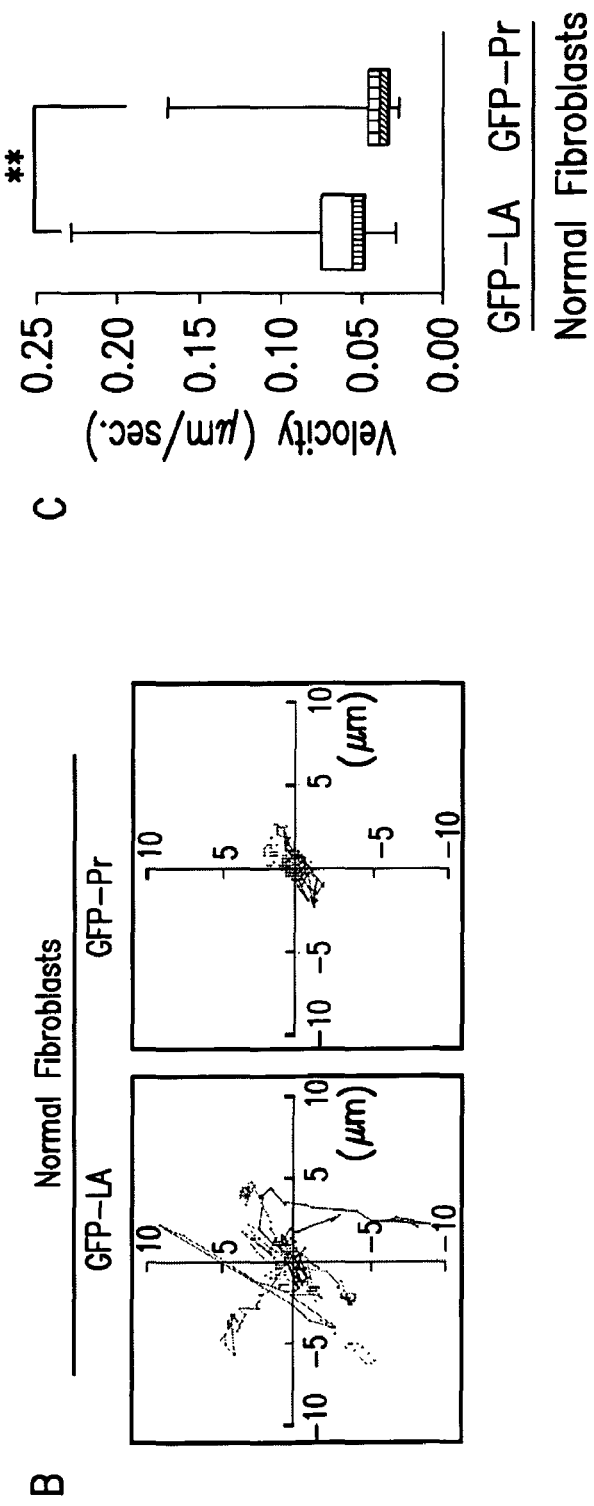

FIG. 7 (A)-(D): Mitochondrial Speed and Travel Analysis for Different Cell Lines: Progerin Expression Affects Mitochondrial Dynamic Behavior
  (A) The results of a study of mitochondrial movement in HGPS cells where mitochondria were labeled with MitoTracker® Green in the two normal and two HGPS fibroblast cells and acquired live cell images at every 10 seconds for a total of 5 minutes, by which intracellular migration of individual mitochondria were tracked.
  (B)-(C) Mitochondria in HGPS cells showed significantly average speeds and shorter travel distances than those in normal cells, and this was further verified in normal cells transduced by lentiviruses expressing either GFP-laminA or GFP-progerin.
  (D) Quantitative RT-PCR showed a significant reduction in expression levels of a few genes involved in mitochondrial fusion and fission in HGPS fibroblasts, including Mfn1, Mfn2, Fis1, Opa1 and Drp1.

Figure 8:
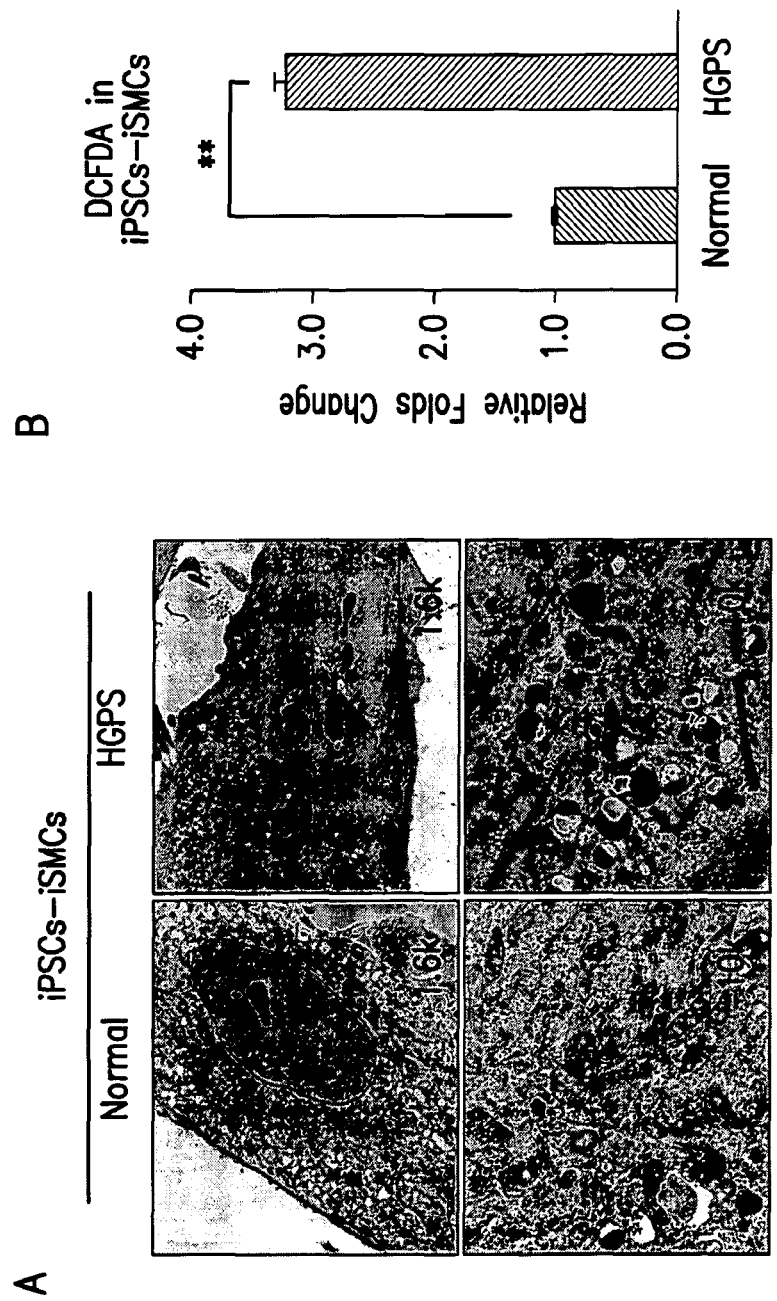

FIG. 8 (A)-(C): Progerin Causes Mitochondrial Structural and Behavioral Abnormalities.
  (A) Enhanced ROS production was detected in HGPS iPSC-differentiated smooth muscle cells (iSMCs).
  (B) HGPS iSMCs showed a profound mitochondrial swollen phenotype under TEM.

Figure 9:
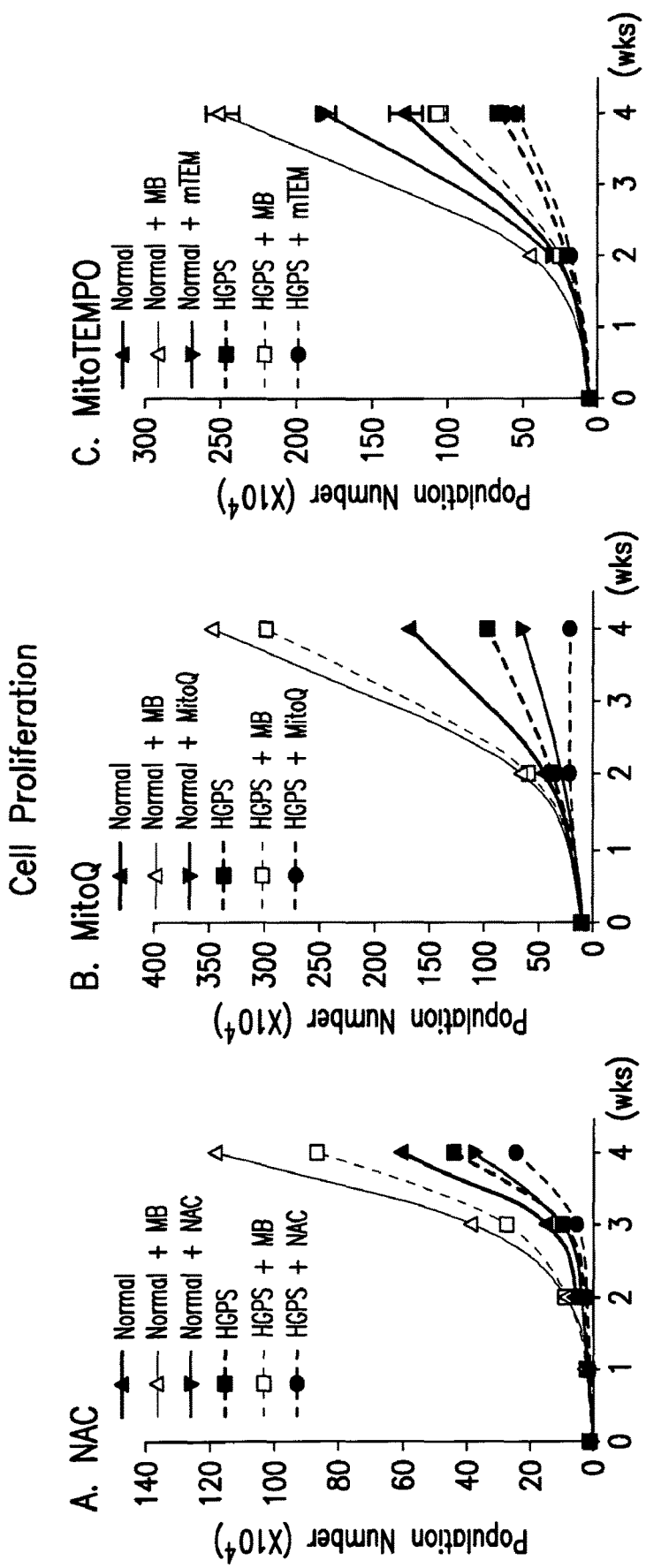

FIG. 9(A)-(C): Comparisons of MB with three different antioxidants NAC (A), MitoQ (B) and MitoTEMPO (C) on cell proliferation indicated significant improvements of cell growth by MB on both normal and HGPS fibroblasts after four weeks treatment (upper panel). The Table beneath provides information for solubility, concentration, and targets in the cell. See line plots (1)-(6).

Figure 10:
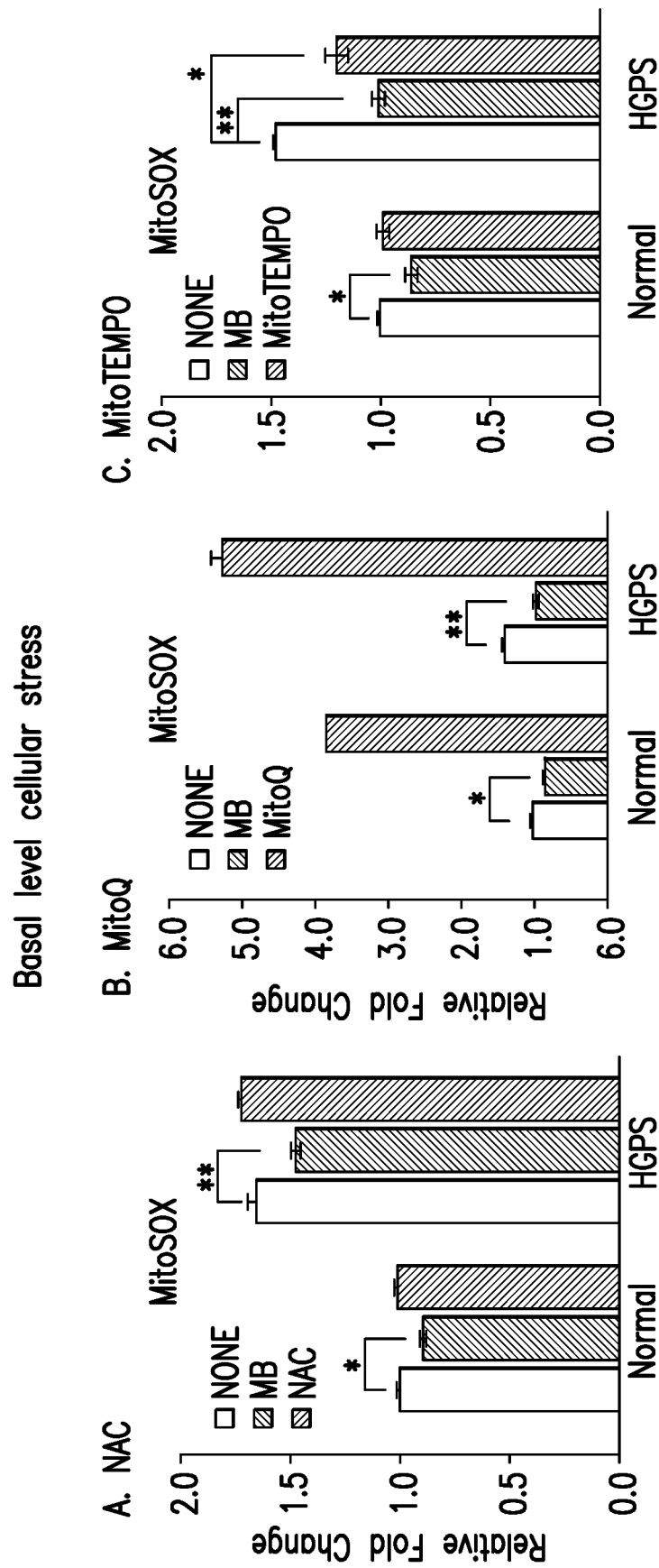

FIG. 10(A)-(C): Basal Level Cellular Stress Compared for three different antioxidants NAC (A), MitoQ (B) and MitoTEMPO (C) on mitochondria specific superoxide (MitoSOX) production indicated a significant decrease of MitoSOX level by MB on both normal and HGPS fibroblasts after four weeks treatment.

Figure 11:
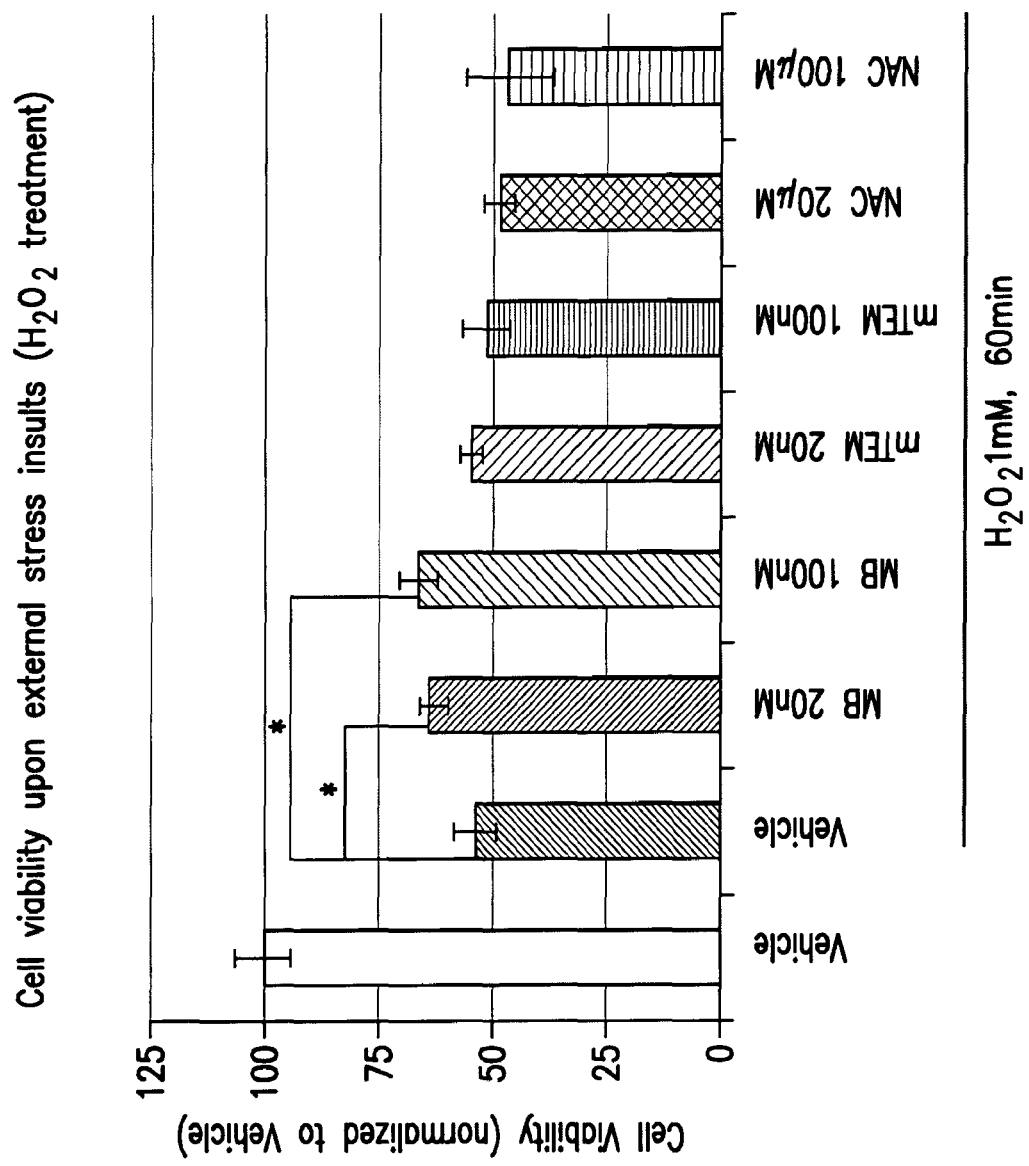

FIG. 11: Cell Viability Upon External Stress Insults (hydrogen peroxide treatment).
  Hydrogen peroxide caused a significant reduction in cell viability, and both low and high concentrations of MB significantly improved cell viability.

Figure 12:
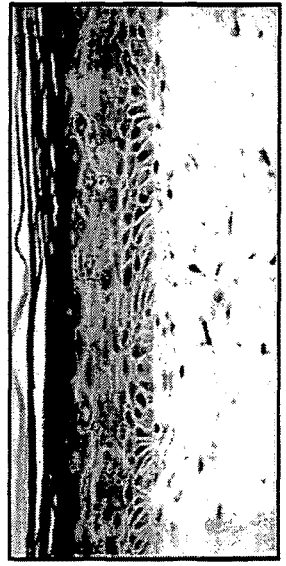
Figure 12:

FIG. 12: 3D Examination of MB Effects On 3D Skin
  A photograph of the 3D skin used in the study is provided.

Figure 13:
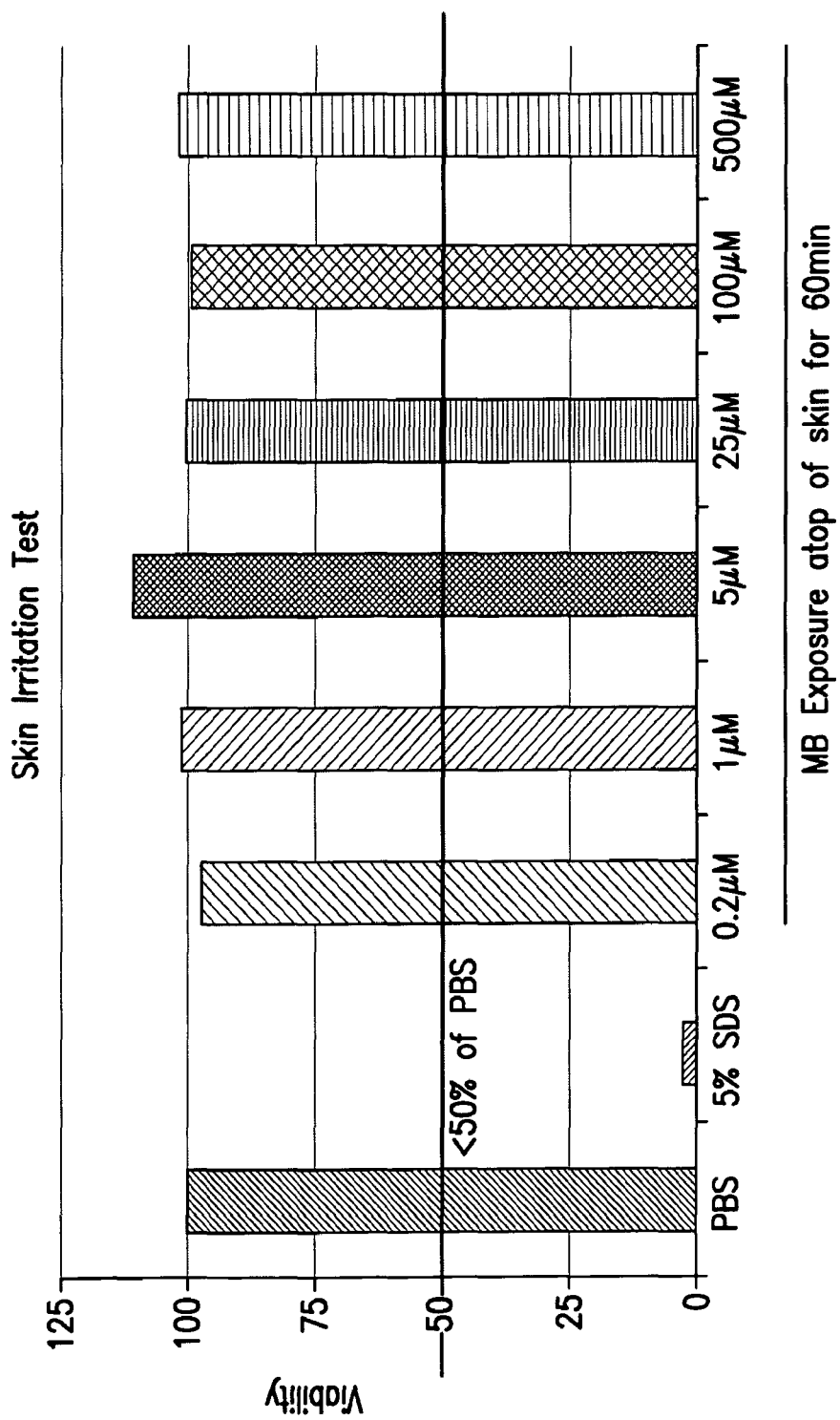

FIG. 13: Skin Irritation Test
  Skin Irritation Test measured by MTT assay on EpiDerm (EPI-200) skin tissue after atop application of MB at various concentrations for 60 minutes. MB showed no skin irritation even at the highest dosage of 500 mM.

FIG. 14: ECM Gene Expression Analysis
  Shows changes in expressions of some skin extracellular matrix genes, AC002094.1, COL2A1, IGK1, KLK3, Elastin, MMP9 and LAMC2, with skin treated with MB at the denoted concentrations for two weeks. The expression of ECM genes were analyzed by quantitative PCR array on EpiDerm Full Thickness (EFT-412).

Figure 15:
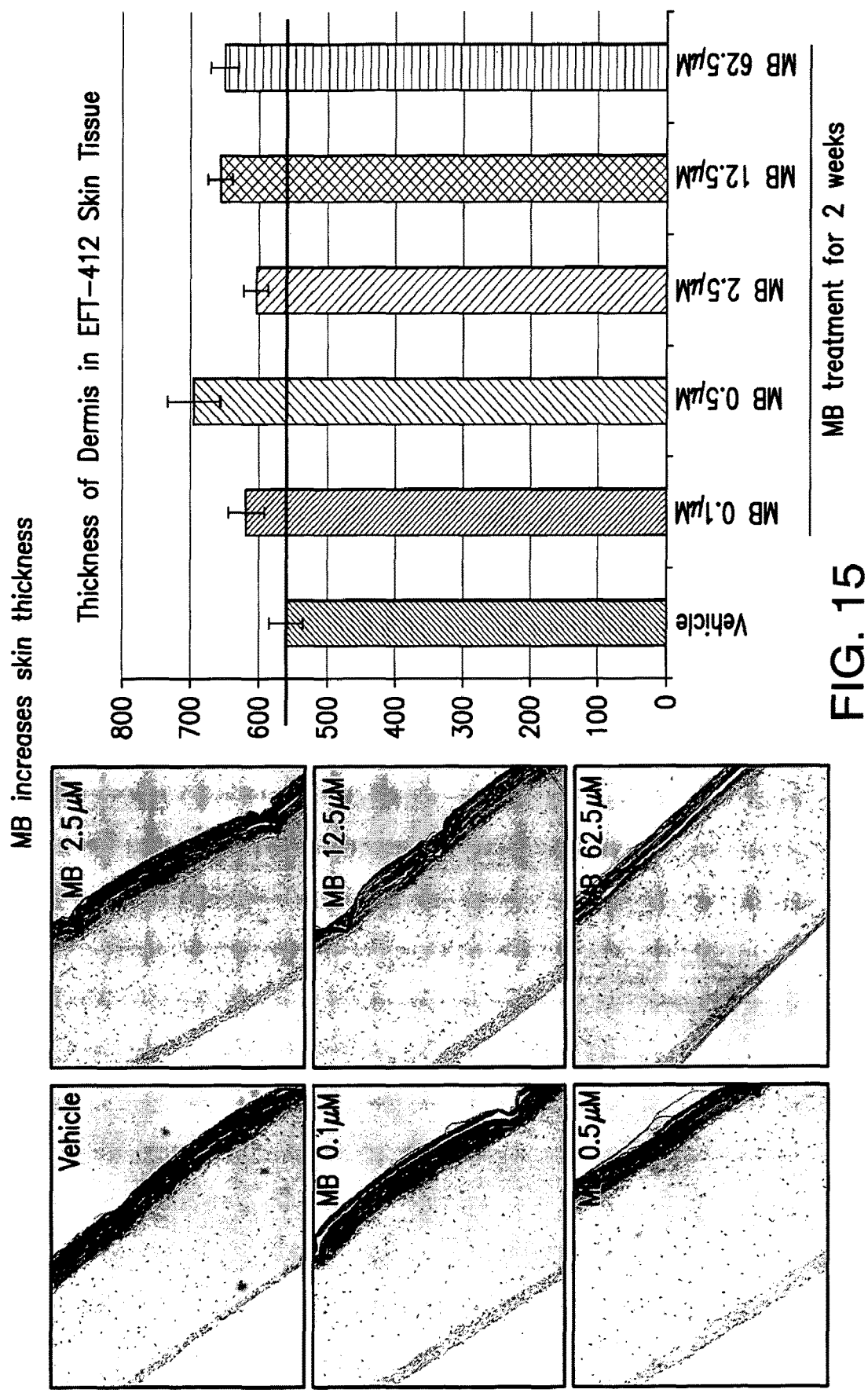

FIG. 15: MB Increases Skin Thickness
  Shows results of Hematoxylin/Eosin (H&E) stained histological cross-section of Epiderm Full Thickness (EFT-412) skin tissue treated with MB at various concentration for two weeks (left).

Figure 16:
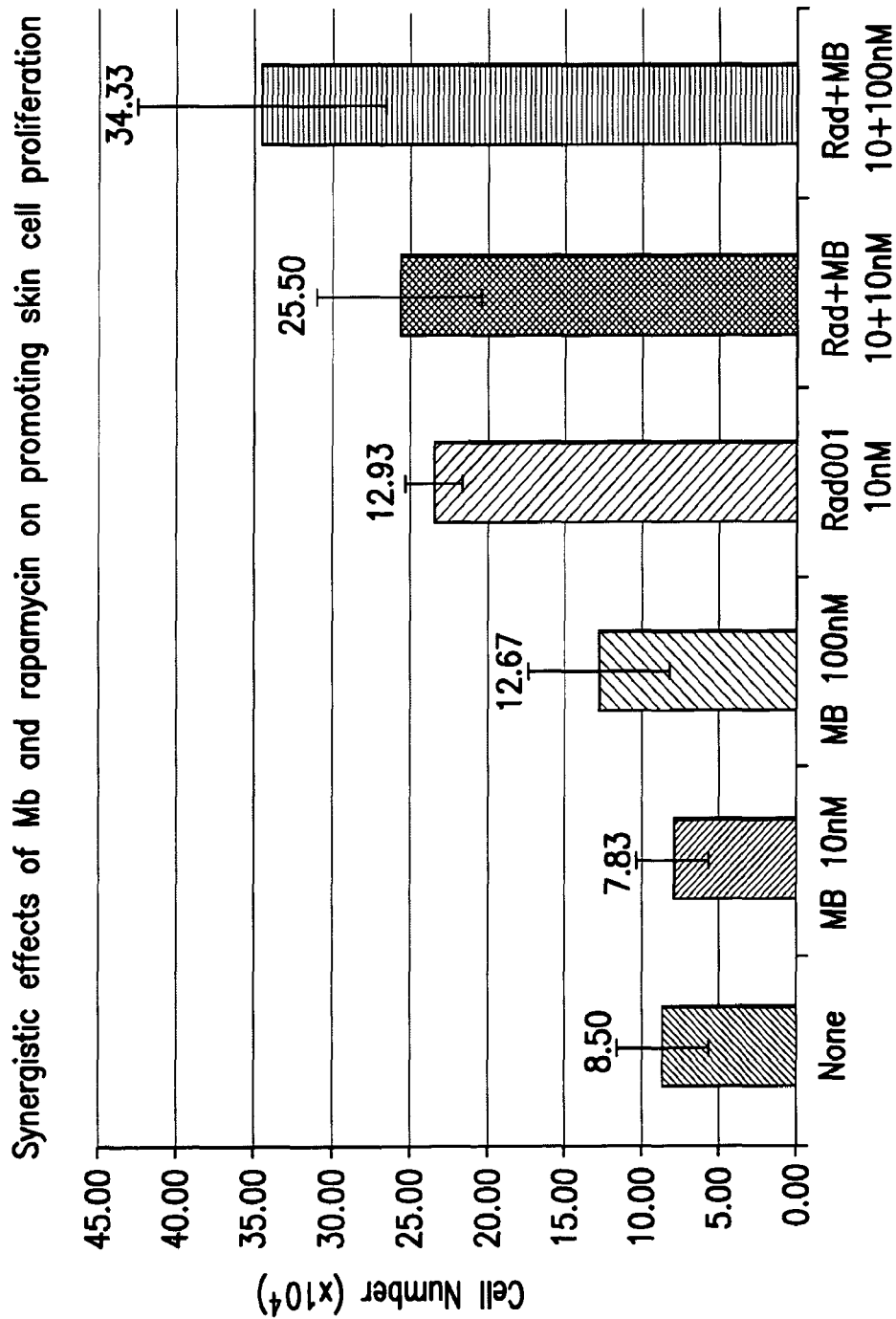

FIG. 16: Combined treatment of low dosage of Rad001 and MB (10 nM+100 nM) synergistically promote cell proliferation on aged human skin fibroblasts.

Figure 17:
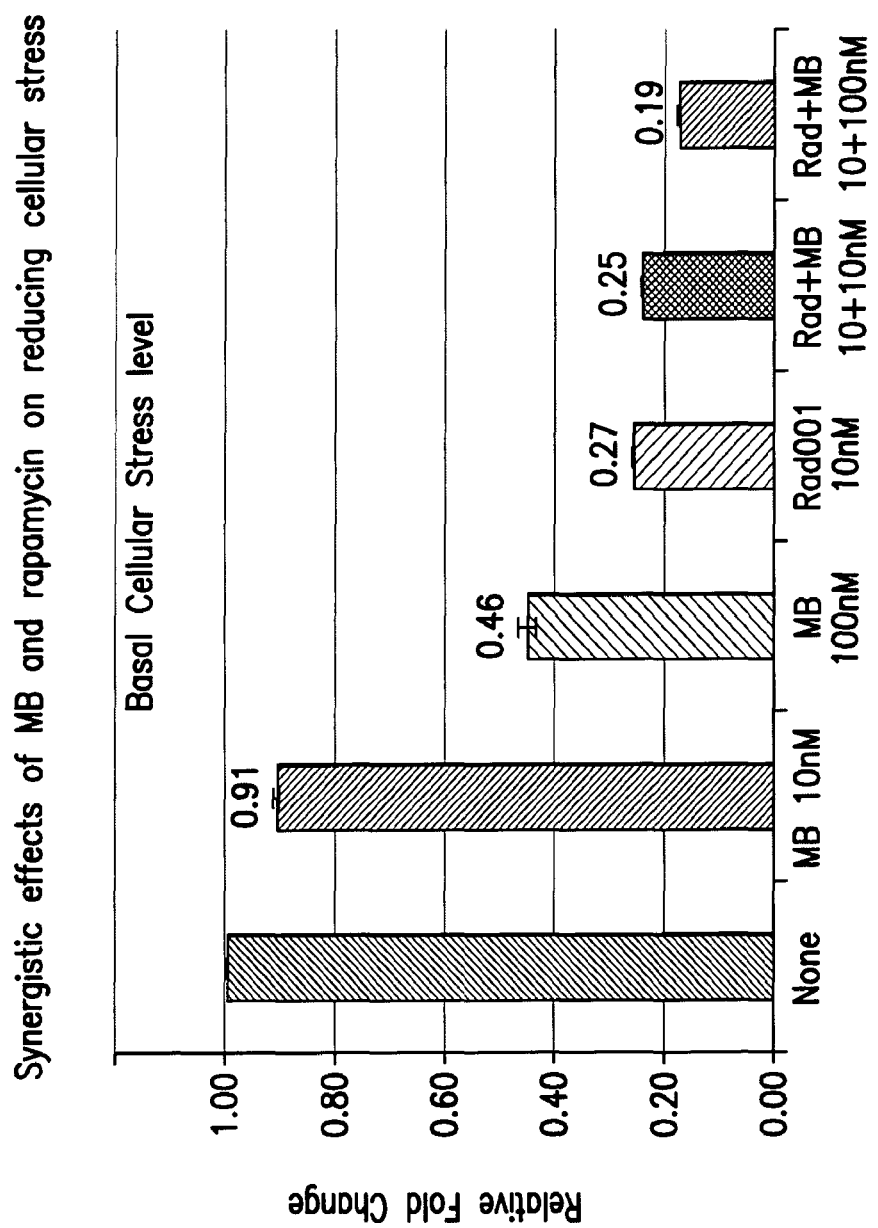

FIG. 17: Combined treatment of low dosage of Rad001 and MB (10 nM+100 nM) synergistically reduced MitoSOX level (basal cellular stress) on aged human skin fibroblasts.

DETAILED DESCRIPTION OF THE PREFERRED EMBODIMENTS

The present invention is based, in part, on the discovery that methylene blue (MB), also known, by IUPAC name, as 3,7-bis(dimethylamino)-phenothiazin-5-ium chloride, an antioxidant which targets mitochondria, alleviates premature aging phenotype and prolongs cellular life span of HGPS cells as well as normal cells.

The present invention is also based, in part, on the discovery that MB may be used by itself or in combination with known mitochondria-targeted antioxidants (MTAs) to alleviate premature aging phenotype and prolong cellular life span of HGPS cells as well as normal cells.

The present invention is also based, in part, upon the discovery that rapamycin and analogues thereof may be used in combination with MTAs, including MB, to decrease formation of insoluble progerin aggregates and induce clearance of the insoluble progerin aggregates through autophagic mechanisms in both HGPS and normal cells. The present invention also provides pharmaceutical compositions containing: MB and an excipient, MB and at least one other MTA compound and an excipient, MB and rapamycin or an analogue thereof and an excipient, and/or MB and at least one other MTA compound and rapamycin or an analogue thereof and an excipient for either alleviating premature aging phenotype in HGPS cells, or alleviating normal aging phenotype in normal cells, or decreasing formation of insoluble progerin aggregates and inducing clearance of the insoluble progerin aggregates through autophagic mechanisms in both HGPS and normal cells.

Term Definitions:

The following terms will be used throughout the specification below, and are defined as follows:

MB: methylene blue, also known as 3,7-bis-(dimethylamino)-phenothiazin-5-ium chloride.

MB derivative: means biologically active methylene blue compounds having the structure shown in U.S. Pat. No. 8,188,074, which is incorporated herein in the entirety. Notably, in all of these compounds, the two dimethylamino groups of MB are replaced by two substituted amino groups as defined in U.S. Pat. No. 8,188,074. Any of these compounds may be used with or instead of MB in the present invention.

HGPS: Hutchinson-Gilford progeria syndrome is a lethal genetic disorder characterized by premature aging, and most commonly caused by a de novo single-nucleotide substitution in the lamin A/C gene (LMNA) that partially activates a cryptic splice donor site in exon 11, producing an abnormal lamin A protein called progerin.

Rapamycin: a macrolide antibiotic produced by *Streptomyces hydroscopicus* known for its potent antifungal, immunosuppressive and anticancer activities, as well as its ability to extend longevity in yeasts, invertebrates and mammals. This antibiotic is also known to activate autophagy in HGPS patients and normal aging patients. The molecular structure of rapamycin is well known. See, for example, Ritacco, et al. Applied and Environmental Microbiology, April 2005, pp. 1971-1976. Rapamycin is also known as sirolimus. The molecular structure of rapamycin is also shown in U.S. Pub. 2008/ 0275076 A1, which patent publication is incorporated herein in the entirety.

Rapamycin analogues: means derivatives of rapamycin including such compounds as 20-thiarapamycin and 15-deoxo-19-sulfoxylrapamycin (see Ritacco, et al., Applied and Environmental Microbiology, Apr. 2005, pp. 1971-1976), 40-O-(2-hydroxyethyl) rapamycin (see Driscoll, et al. Aging, February 2012, Vol. 4, No. 2), C-20-methylallylrapamycin, C16(S)-butyl-sulfonamidorapamycin, C16-(S)-3-methylindolerapamycin, C16-(S)-methyl-indolerapamycin (see Crabtree, et al. Chemistry and Biology 13, 99-104, January 2006) and the tetrazole-containing rapamycin compounds of U.S. Pat. No. 6,329,386, which patent is incorporated herein in the entirety. Thus, the term rapamycin analogues includes not only analogues having various substituent groups attached to rapamycin rings, but also analogues in which various rapamycin rings contain heterocylic atoms, such as S, or functional groups, such as S═O. Further, U.S. Pat. No. 5,665,772, which discloses O-alkylated rapamycin derivatives, is incorporated herein in the entirety. All of the compounds defined herein as rapamycin analogues are substituted rapamycins, either by substituent groups bonded to any of the rapamycin rings or by heteroatoms substituted in place of carbon atoms in any of the rapamycin rings.

Mitochondria-targeted antioxidants: means antioxidant compounds that generally contain a cationic portion in the compound that targets mitochondria due to the known negative membrane potential (about −150 mV) of mitochondria. Examples of MTAs include TPP+(triphenylphosphonium ion) containing lipophilic antioxidants, such as MitoQ (conenzyme Q), Mitovitamin E, and Szeto-Schiller (SS) compounds which are tetrapeptides with an alternating aromatic cationic amino acids motif. See U.S. Pat. No. 7,576,061 B2, which is incorporated herein in the entirety. Other TPP+antioxidants that may be used are MitoTEMPOL, MitoPBN, MitoPeroxidase, MitoSOD, and MitoApocyanin. Particular Szeto-Schiller compounds of note are the known compounds SS-31, SS-20 and XJB-5-131, whose molecular structures shown by Jin, et al. Biochimica et Biophysica Acta 1842 (2014) 1282-1294. Also included in this definition is methylene blue (MB) and derivatives thereof as defined above under MB derivative.

Composition: includes all forms that may vary according to use, such as pharmaceutical, cosmetic, dermatological, or skin care or soap, and which necessarily include uses that alleviate or mitigate symptoms of aging, regardless of whether caused by HGPS or normal aging.

Topical composition: means a composition formulated to be administered by being applied to the skin. This may include a large variety of physical forms, including lotions, gels, sprays and dry powders that are absorbable into the skin, ointments, drops and transdermal patches. Topical formulations may be used as described in U.S. Pub. 2012/ 0022095 A1, for example, which published patent is incorporated herein in the entirety.

Injectable pharmaceutical composition: means a pharmaceutical composition formulated to be administered by injection, such as intravenous, intramuscular and intraperitoneally, for example. Injectable formulations may be used, for example, as described in U.S. Pat. No. 5,530,006, which patent is incorporated herein in the entirety.

Oral composition: means a composition formulated to be administered orally, such as syrups, tablets, capsules or lozenges, for example. Injectable formulations may be used, for example, as described in U.S. Pat. No. 5,989,591, which patent is incorporated herein in the entirety.

Composition: means any composition without restriction as to form as may be determined by use. Thus, the term "composition" necessarily includes pharmaceutical compositions, dermatological compositions, skin care compositions, injectable compositions or soaps, for example.

Cosmetic Composition: means a composition formulated for skin care, and which includes, for example, make-up compositions and moisturizing creams or lotions, or soaps. See U.S. Pat. Pub. 2013/0243714 A1, and U.S. Pat. No. 5,547,602 A, respectively, both of which are incorporated herein in the entirety.

Aging Phenotype: means observable, physiological symptoms associated with aging, including hair loss, bone deficits and loss of skin flexibility. While children with HGPS display many of the phenotypes associated with normal aging, these symptoms occur at a very early age for HGPS children. Yet, even normal cells accumulate increasing amounts of progeria that increase with age. The term "aging phenotype" is used herein as being synonymous with "age-related symptoms" which refers to all manifest symptoms of aging including, but not limited to accumulation of progerin in cells, wrinkles, hair loss, bone deficits, loss of skin elasticity and tone, and even cognitive decline, macular degeneration and dementia.

Pharmaceutically-acceptable carrier or excipient: means a non-toxic solid, semi-solid or liquid filler, diluent, encapsulating material or formulation auxiliary of any type. Exemplary carriers or excipients from U.S. Pub. 2008/0275076 A1 and U.S. Pat. No. 8,313,763 B2 may be used as carriers or excipients with the present invention. Both U.S. Pub. 2008/0275076 A1 and U.S. Pat. No. 8,313,763 B2 are incorporated herein in the entirety. Of course, specific formulations may require suitable excipients, for example, oral formulations may advantageously use the excipients disclosed in U.S. Pat. No. 5,989,591; injectable formulations may advantageously use the excipients disclosed in U.S. Pat. No. 5,530,006; and topical formulations may advantageously use the excipients disclosed in U.S. Pub. 2012/0022095 A1.

RAD001: is everolimus, which is 40-O-(2-hydroxylethyl) rapamycin. Rapamycin is also known as sirolimus.

Abbreviations Used Herein:
HGPS: Hutchinson-Gilford Progeria Syndrome
PGC-1α: peroxisome proliferator-activated receptor gamma coactivator 1-alpha
PPARγ: peroxisome proliferator-activated receptor gamma
NRFs: nuclear reparatory factors
TRAM: mitochondria transcription factor A
ROS: reactive oxygen species
iPSC: induced pluripotent stem cell All of the compounds described for use in this application are either commercially available or are otherwise known as evidenced by U.S. patents.

The present invention may simply entail the administration of MB to alleviate symptoms of aging in both HGPS mammals, particularly humans; and in normally aging mammals, particularly humans. However, the present invention will more often entail the administration of pharmaceutical compositions.

The pharmaceutical compositions of the present invention may contain just MB as an active ingredient and a pharmaceutically-acceptable excipient; or it may contain MB and one or more other MTA compounds, such as TPP+compound, and an excipient; or it may contain MB alone or with one or more other MTA compounds, and rapamycin or an analogue thereof, and an excipient. Of note, however, is that all of the pharmaceutical compositions of the present invention contain MB as one of the active ingredients.

While the present pharmaceutical compositions are preferably topical formulations, the compositions may also be formulated to be administered orally, rectally, parenterally, intracisternally intravaginally, and intraperitoneally. Any of the excipients described in U.S. Pat. No. 6,329,386 B2 may be used. Further, the present compositions may be formulated to either singly emphasize repair of mitochondria using mitochondria-targeted antioxidants, particularly MB, or to equally emphasize both repair of mitochondria with mitochondria-targeted antioxidants and clearance of progerin from either progeria or natural aging with rapamycin or one or more rapamycin derivatives. Yet, in all cases MB or one or more MB derivatives are included in the formulations. Both Methylene blue and rapamycin are commercially available.

Generally, the compositions of the present invention contain MB in an amount of about 10 micrograms to about 1,000 micrograms (or 1 mg) per unit dose per kilogram of body weight of the mammal, particularly a human. Thus, for a human patient having a weight of 100 kgs, a unit dose of MB of from 1 mg to 100 mg may be used. The actual dosage and frequency of administration may be determined and regulated by a physician.

Furthermore, any one or more of the MB derivatives as defined in this application may be used in the formulation with MB with the total amount of MB and all MB derivatives being within the range of about 10 micrograms to about 1,000 micrograms or 1 mg per unit dose per kg of body weight of the mammal, particularly a human. These amounts are applicable for any mode of administration, i.e., topical, oral or by IV, for example.

If the composition also contains rapamycin and/or one or more rapamycin derivatives as defined herein, the composition contains rapamycin and one or more rapamycin derivatives in amounts dependent upon the mode of administration. Generally, for oral administration, single dosage forms contain from about 0.05 to 20 mg of rapamycin and/or one or more rapamycin derivatives. Generally, for topical administration, topical formulations contain about 0.1 to 5% by weight, and more preferably from about 0.25 to 2% by weight. Generally, for IV administration, IV suitable formulations contain from about 0.25 to 100 micrograms per ml of injectable solution. For all forms of administration, however, the precise dosage and frequency of administration will depend upon the discretion of the treating physician.

Generally, carriers or excipients for topical formulations may include solvents, lubricants, emollients, emulsifiers, moisturizers, thickening wax, softeners, fragrances, preservatives and artificial or natural coloring agents, for example.

Generally, carriers or excipients for oral formulations may include surfactants, and binders, such as poloxomer 188, sucrose, povidone, microcrystalline cellulose and water, for example.

Generally, carriers or excipients for IV formulations may include water, N,N-dimethylacetamide, polyxyethylene sorbitan esters, and polyethylene glycol, for example.

Having described the present invention, reference is made below to certain examples which are provided solely for purposes of illustration are not intended to be limitative.

In the examples below, MitoTracker® will be referred to below as MitoTracker. Its status as a trademark is acknowledged here.

EXAMPLE 1

Progerin Expression Induces Swollen and Fragmented Mitochondria and Inhibits Mitochondrial Mobility Mitochondria have variable morphologies classified as reticular, intermediate or fragmented according to their shape and size. This morphological diversity has linked to mitochondrial function. To visualize mitochondria in live cells, mitochondria were stained with MitoTracker and mitochondrial morphologies in two HGPS and two normal cell lines (Normal-1 and Normal-2) (details in Materials) were compared. In both normal cell lines, we observed perinuclear reticular mitochondrial network as well as a small fraction of intermediate and fragmented mitochondria (FIG. 1A). However, in both HGPS cells, a drastic increase of fragmented mitochondria were observed, with this phenotype being even more severe in one HGPS line (HGPS-2) than the other (HGPS-1) (FIG. 1A). In HGPS-2, we observed not only fragmentation but also swollen mitochondria and a complete loss of perinuclear reticular network (FIG. 1A). Western blotting analysis verified the expression of progerin in HGPS-1 and HGPS-2 cells. HGPS-2 showed a much higher expression of progerin than HGPS-1. T reduce phenotype variations caused by genetic background and directly verify the effect of progerin on mitochondrial morphology, we transduced a normal fibroblast cell line (Normal-1) with GFP-lamin A or GFP-progerin lentiviruses. Two weeks after transduction, we found that the GFP-progerin-expressing cells exhibited a similar mitochondrial fragmentation phenotype as that in primary HGPS fibroblasts, and most of these fragmented mitochondria appear to be circular and swollen (FIG. 1B). Based on this observation, we conclude that the expression of progerin leads to fragmented and swollen mitochondria.

To elucidate these mitochondrial defects at a high resolution, next, we applied transmission electron microscopy (TEM) technology in normal-1 and HGPS-1 fibroblasts. To quantify various mitochondrial abnormalities, we set up three general categories for phenotype grading according to the intactness of membrane (outer, inner and cristae), matrix integrity and overall organelle shape: mitochondria with intact membrane and matrix are considered as "Normal" (FIG. 1C, a-b); mitochondria with broken membrane or with small vacuole areas in matrix (less than 20% of the total area) are considered as "Minor Defects" (FIG. 1C, c-d); and mitochondria that are either morphologically abnormal (swollen or budding), or with large vacuole areas are defined as "Severe Defects" (FIG. 1C, e-h). According to these criteria, we found that both normal and HGPS fibroblasts had similar percentages of mildly defective mitochondria. However, there was a two-fold increase in severely defective mitochondria in HGPS fibroblasts compared to normal cells (approximately 40% vs. 20%, FIG. 1D).

Mitochondrion, as a vulnerable target of reactive oxygen species (ROS), usually demonstrates a small amount of abnormal phenotypes under the normal physiological condition, for example, normal aging. These morphological changes, including disappeared cristae, disrupted membrane or small vacuole formation in matrix are quite similar to what we categorized here as "mild defects". However, in HGPS cells, approximately one half of the mitochondria show extremely phenotypes, including abnormal budding(s), swollenness and extensive loss of matrix, which provide a structural basis for mitochondrial functional defects and may even be considered as one of cellular characteristics of HGPS cells.

EXAMPLE 2

Figure 2:
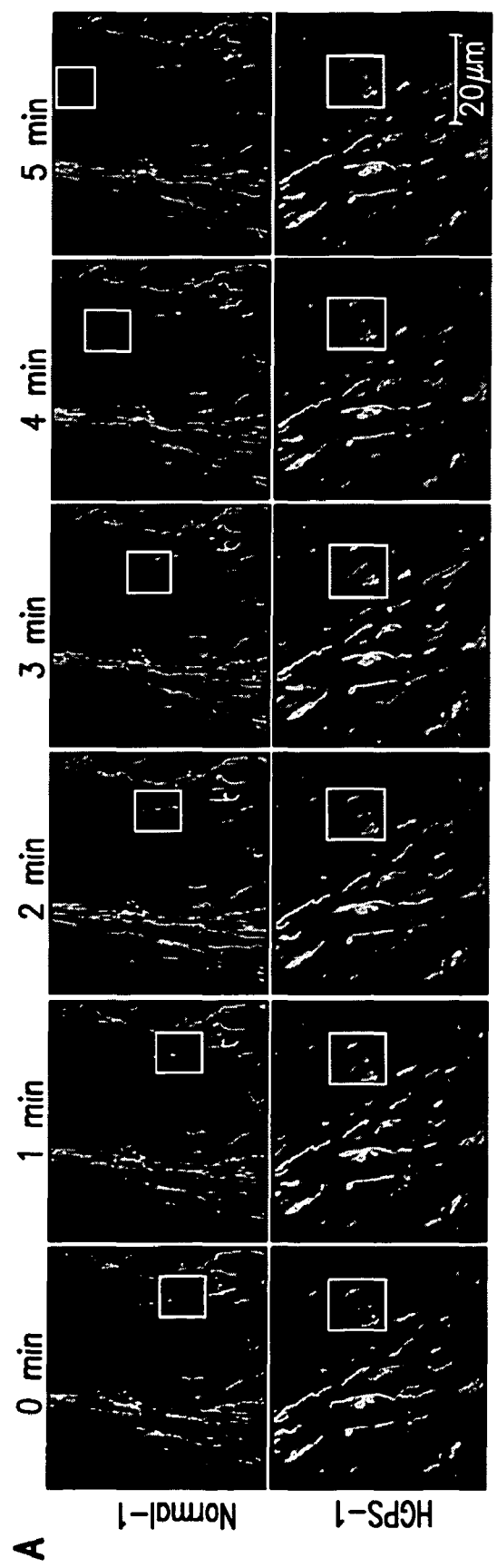
FIG. 2(A-G) Defective mitochondria mobility and function in HGPS fibroblasts
- (A) Time-lapse images of mitochondria labeled with MitoTracker Green FM in normal-1 or HGPS-1 cells. Images were acquired every 10 seconds over a total of 5 minutes time course by a spinning disk confocal microscope.
- (B) Movement traces of 10 representative mitochondria per each cell line in two normal fibroblast lines and two HGPS fibroblast lines. Different colors represent individual mitochondria, and each dot shows one acquired time point at 10 second intervals.
- (C) Velocity quantification of mitochondrial movement in two cell lines from each of normal and HGPS fibroblasts. Sixty mitochondria per cell line were randomly selected for velocity analysis ($**p<0.01$)
- (D) Relative fold change of mitochondrial superoxide (MitoSOX, left) and intracellular ROS (DCFDA, right) amounts measured by FACS analysis in normal-1 and HGPS-1 fibroblasts ($**p<0.01$).
- (E and F) Relative cell percentages with disrupted mitochondrial membrane potential (MMP,E) and apoptosis (F) ($**p<0.01$)
- (G) ATP production in two normal and two HGPS fibroblasts ($*p<0.05$).
Figure 2:
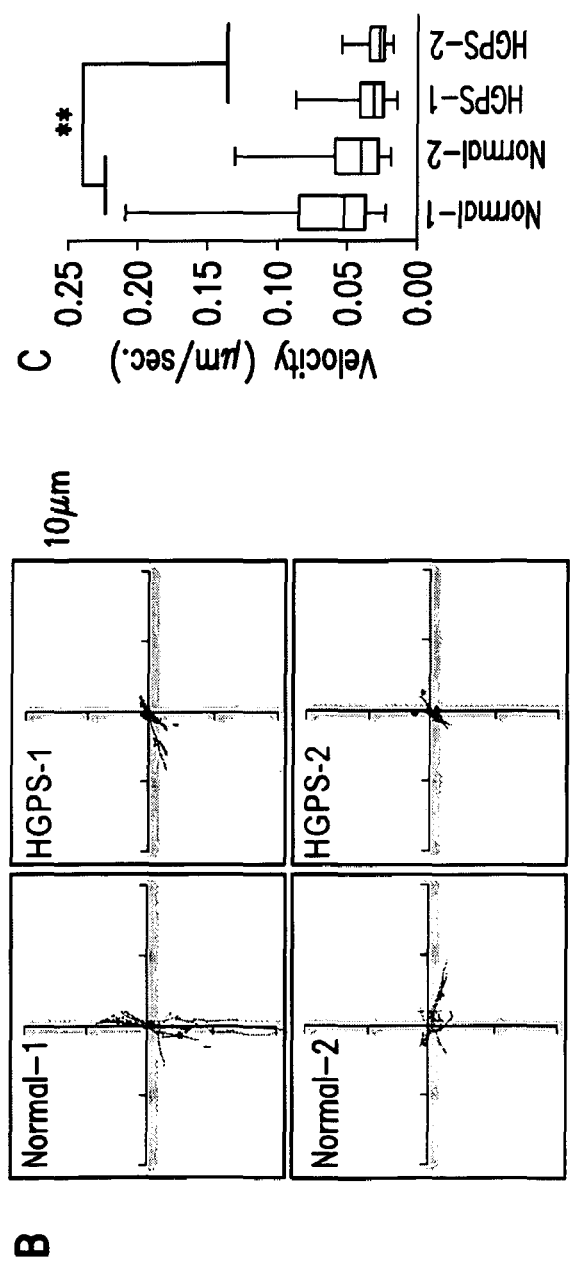
Figure 2:
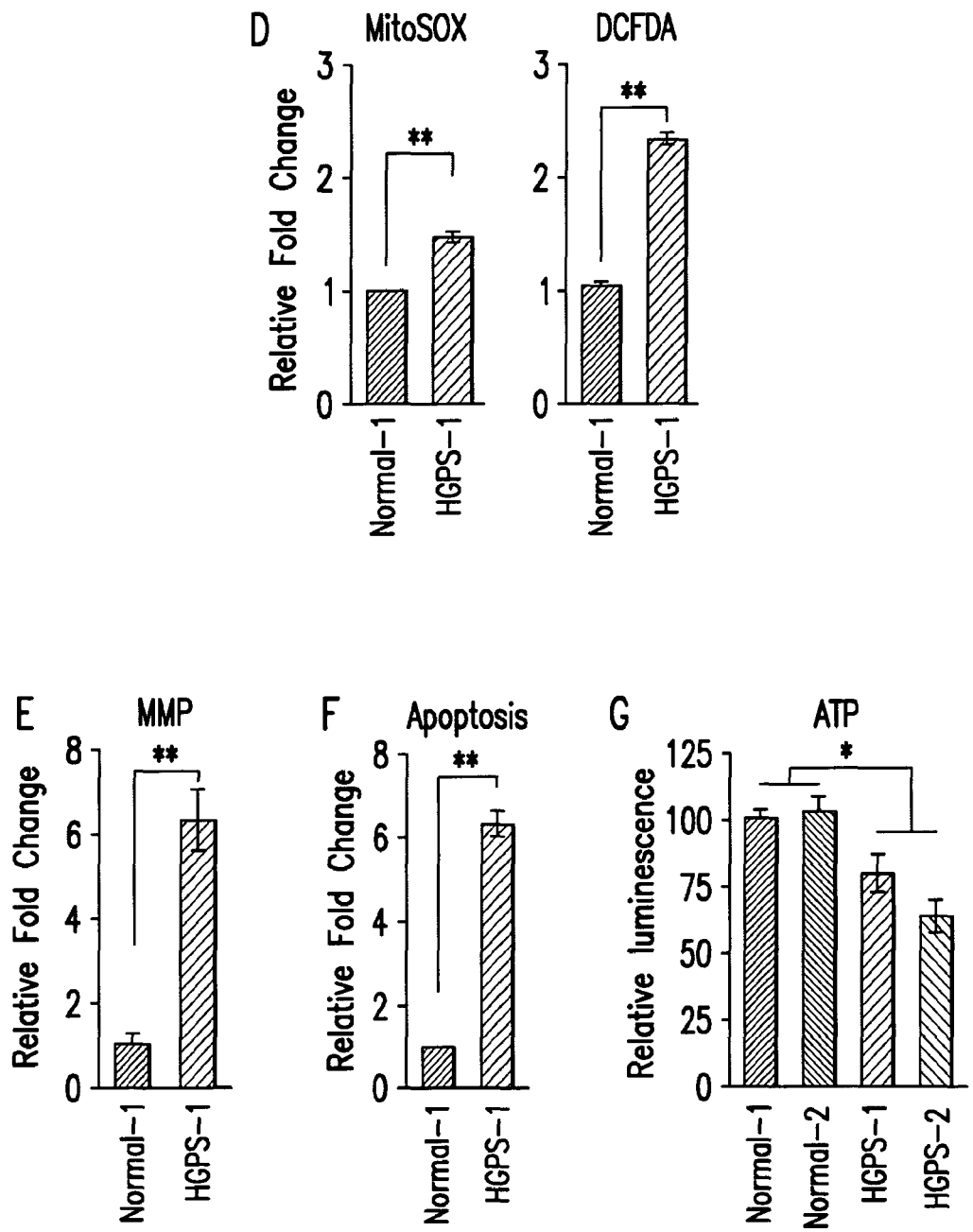

Defective Mitochondrial Behavior in HGPS Fibroblasts; Mitochondria in Progerin Expressing Cells Show Impaired Function Mitochondrion travels long distance in the cells, along the cytoskeleton. This movement controls mitochondrial shape, intracellular distribution, biogenesis and function. To investigate mitochondrial movement in HGPS cells, we labeled mitochondria with MitoTracker Green in the two normal and two HGPS fibroblast cells and acquired live cell images at every 10 second interval for total 5 minutes, which allowed us to track intracellular migration of the individual mitochondrion (FIG. 2A). A total of 60 mitochondria from each cell line were randomly selected for moving speed and travel distance analysis. Interestingly, the mitochondria in HGPS cells showed significantly slower average speed and shorter travel distance than those in normal cells (FIGS. 2B & C). This observation was further verified in normal cells transduced by lentiviruses expressing either GFP-lamin A or GFP-progerin. Furthermore, quantitative RT-PCR revealed significantly reduced expression levels of a number of genes involved in mitochondrial biogenesis in HGPS fibroblasts, including fusion-related genes (Mfn2 and Opa1) and fission-related genes (Drp1 and MTP18). Taken together, these findings suggest that progerin expression affects mitochondrial dynamics.

Previous evidence suggested an elevated basal level of cellular ROS in HGPS cells. We measured the overall intracellular ROS by DCFDA and the mitochondrial specific superoxide by mitoSOX and found that both were significantly elevated in HGPS fibroblast cells (FIG. 2D). Moreover, enhanced ROS production was detected in HGPS iPSC-differentiated smooth muscle cells (iSMCs). These HGPS iSMCs showed a profound mitochondrial swollen phenotype under TEM, further supporting the notion that progerin expression leads to mitochondrial structural and behavior abnormalities.

Moreover, an increase in cells with mitochondrial membrane potential (MMP) disruption and apoptosis (FIG. 2E-F) as well as a reduction in cellular ATP production (FIG. 2G) were also observed in HGPS samples.

Together, these results support a model that progerin causes structural and behavior abnormalities in mitochondria, which may further lead to elevated ROS production and impaired oxidative phosphorylation. As a part of the vicious cycle between mitochondria and ROS, a decline in mitochondrial function leads to enhanced ROS production, which results in further damage to mitochondria as well as other cellular components.

EXAMPLE 3

Progerin Suppresses PGC-1α Expression

PGC-1α serves as a master inducer of mitochondrial biogenesis through its coactivation of nuclear respiratory factors (NRFs), which control the expression of nuclear genes encoding mitochondria proteins. Using adipogenesis array, we previously reported that in HGPS adipocytes, PGC-1α was the most severely downregulated gene among the 84 genes involved in energy metabolism. To understand how progerin causes mitochondrial defects, we first examined PGC-1α in primary HGPS fibroblasts.

Figure 3:
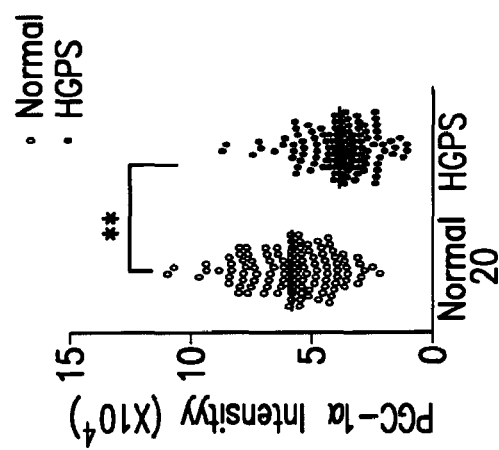
FIG. 3(A)-(G) Reduced PGC-1α in HGPS cells.
- (A) Quantitative RT-PCR analysis of PGC-1α expression in two normal and two fibroblast cell lines ($**p<0.01$).
- (B) Representative immunofluorescence images of normal-1 and HGPS-1 fibroblasts (as Normal and HGPS hereinafter) stained with anti-lamin A/C and anti-PGC-1α antibodies.
- (C) Western blotting analysis with anti-PGC-1α, anti-lamin A/C or anti-β-actin antibodies in normal and HGPS fibroblasts (two technical replicates per each fibroblast). Arrow points to progerin protein. The black dotted line indicates that the normal and HGPS bands have been spliced together from the same film.
- (D) Quantitative RT-PCR analysis of Nrf1, Tfam1, Mfn1, Mfn2, Opa1, Fis1 and Drp1 in normal and HGPS fibroblasts ($**p<0.01$).
- (E) Western blot analysis with anti-PGC-1α, anti-lamin A/C and anti-β-actin antibodies in normal fibroblasts transduced with lentivirus expressing GFP-lamin A (GFP-LA) or GFP-progerin (GFP-Pr).
- (F) Western blot analysis with anti-PGC-1α confirmed the exogenous expression of His-tagged human PGC-1α in HGPS fibroblasts infected with lentivirus containing His-tagged human PGC-1α genes for three days (upper panel). Lentivirus containing lamin A gene (LA) was used as a control here. The black dotted line indicates that the bands have been spliced together from the same film. The MitoSOX were checked by FACS analysis in the same fibroblast cells (lower panel).
- (G) Representative cell images of mitochondria in either LA or PGC-1α lentiviral-infected HGPS cells.
Figure 3:
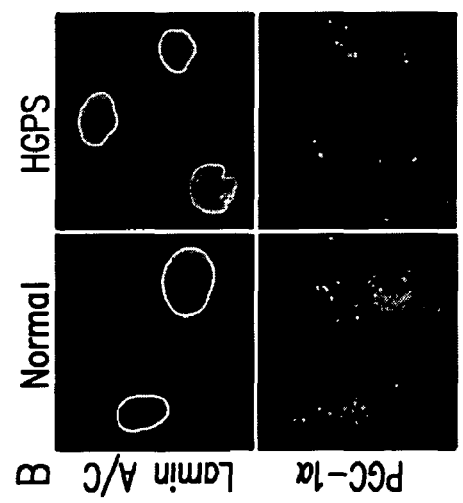
Figure 3:
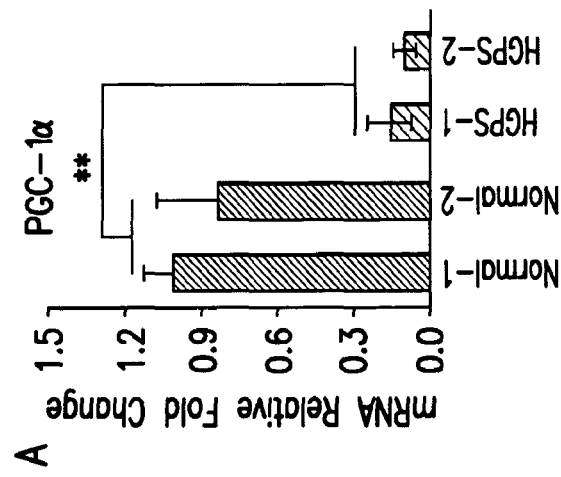
Figure 3:
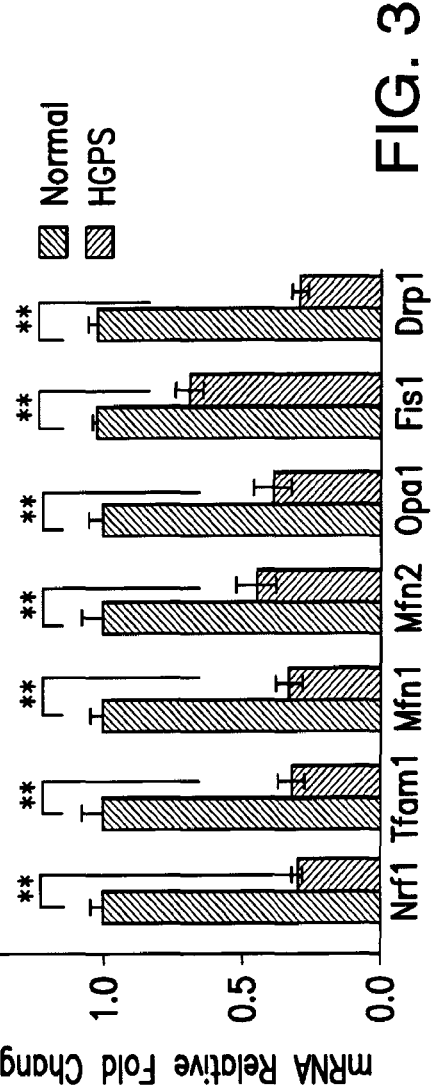
Figure 3:
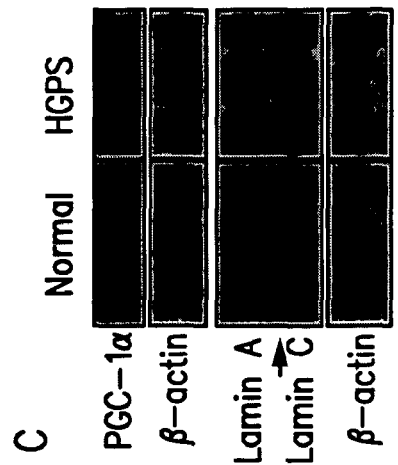
Figure 3:
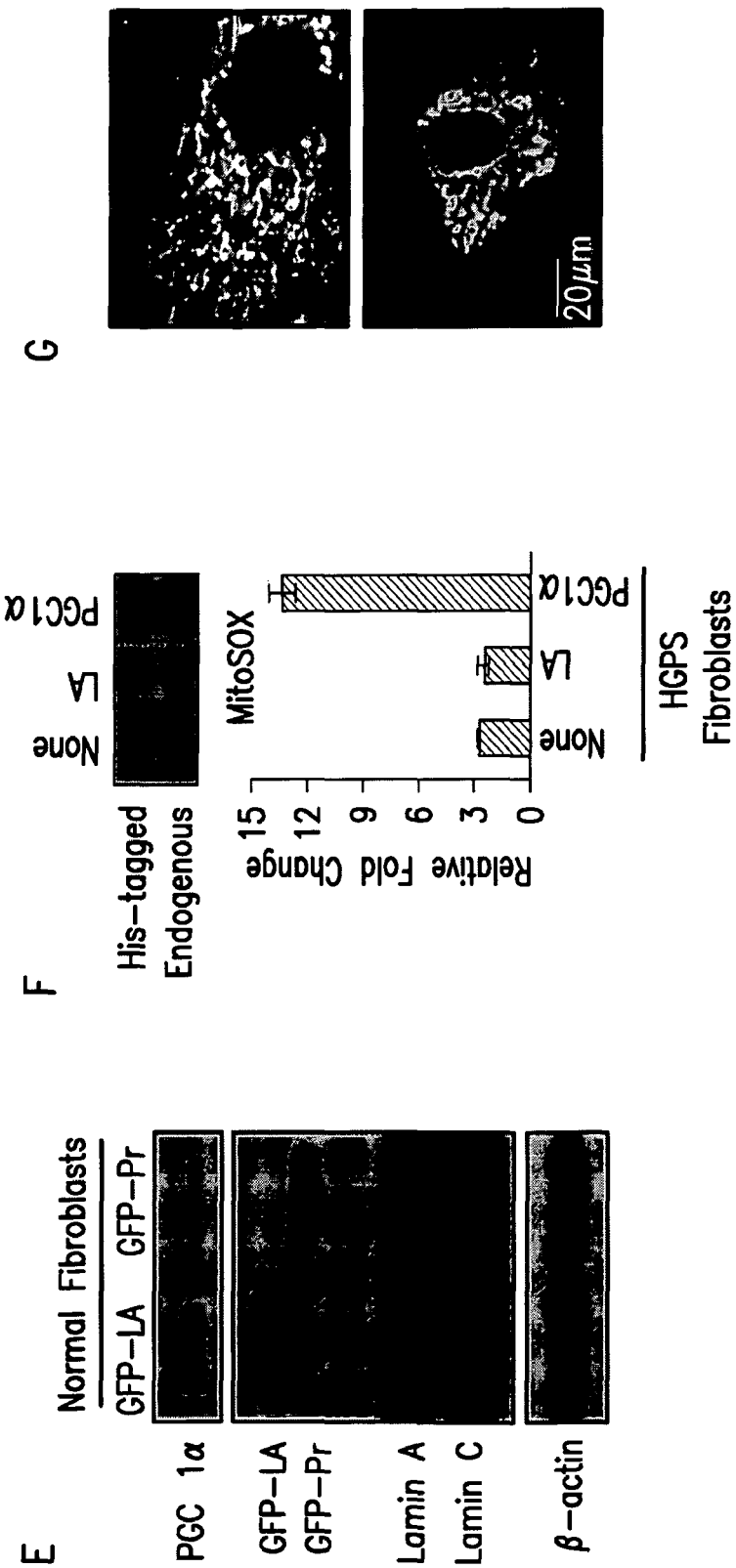

Quantitative RT-PCR experiments revealed that the PGC-1α mRNA level declined by eight fold in HGPS cell lines compared to normal cell lines (FIG. 3A).

Immunofluorescence staining with an anti-PGC-1α antibody revealed that while normal fibroblasts showed uniform nuclear staining of PGC-1α, HGPS cells exhibited either weakened or completely loss of nuclear staining (FIG. 3B). Quantification of PGC-1α staining fluorescence intensity in over 100 cells indicated a significant reduction in PGC-1α nuclear staining in HGPS cells compared to normal fibroblasts (FIG. 3B). This reduction was at least partially regulated at the transcriptional level. RT-PCR experiments revealed that PGC-1α mRNA level is proximately 8-fold lower in two HGPS cells compared to two normal cells (FIG. 3C). This was confirmed by Western blot analysis. In addition, we found that the adaptive stimulation response of PGC-1α upon serum starvation for 24 hours was partially defective, as we only detected a milder response of a 9-fold increase in HGPS cells compared to an over 22-fold induction in normal cells (FIG. 3D). The inhibition of PGC-1α by progerin was confirmed using lentiviruses expressing either GFP-lamin A or GFP-progerin. 18 days after virus induction, we detected a clear decrease of PGC-1α protein in normal fibroblasts transfected with GFP-progerin (FIG. 3E). To test whether restoration of PGC-1α in HGPS cells alleviates the mitochondrial defects, lentivirus carrying either a control lamin A gene (LA) or human PGC-1α gene were applied to HGPS fibroblast cells (FIG. 3F). Surprisingly, no apparent improvements in mitochondrial morphology or behavior were detected (representative cell images are shown in FIG. 3F). Taken together, these results suggest that while PGC-1α has an established role in regulating mitochondrial biogenesis, correction of PGC-1α expression alone might not be sufficient to rescue the severe mitochondrial phenotypes caused by progerin.

EXAMPLE 4

MB Promotes Cell Proliferation and Rescues Hallmark Nuclear Blebbing Phenotype in GPS Fibroblasts MB is known to inhibit age-related decline in cognitive function and grip strength at nanomolar concentrations. It also exhibits potent antioxidant effects in mitochondria due to its redox property. The cycling between reduced (MBH2) and oxidized (MB) forms facilitates electron transfer, thus preventing electron leakage, increasing mitochondrial oxidative phosphorylation and reducing ROS overproduction under pathological conditions. Based on this existing knowledge, treatment of HGPS cells with MB was examined to determine if such treatment could alleviate dysfunctional mitochondria and delay premature senescence.

To test the in vitro effects of MB on HGPS cells, HGPS and normal fibroblasts were treated with MB at 100 nM for 12 weeks. Consistent with previous results MB treatment significantly improved cell proliferation in normal fibroblasts as measured by cell proliferation assay (FIG. 4A). As expected, the HGPS cells grew much slower than normal cells and stopped proliferating after nine weeks' culture. However, the MB-treated HGPS cells continued to proliferate until 12 weeks when we stopped culturing, and its proliferation rate was similar to the untreated (mock-treated) normal cells at the time of culture termination (FIG. 4A). Consistent with the cell proliferation analysis, both senescence-associated-β-galactosidase (SA-β-gal) assay and p16 expression analysis showed that MB-treated HGPS cells were younger than the mock-treated cells. Nuclear blebbing has been considered the hallmark phenotype in HGPS cells, resulting from the abnormal anchorage of progerin to the inner nuclear membrane. To assay the effects of MB on nuclear morphology, mock and MB-treated cells were immunostained with anti-lamin A/C and anti-progerin antibodies (FIG. 4B). It was found that the mean negative curvature, a direct measure of abnormalities of the nuclear shape, was significantly decreased in HGPS cells after MB treatment (FIG. 4C). Thus, it was concluded that MB treatment remediates cell proliferation and nuclear morphology defects in HGPS cells.

EXAMPLE 5

MB UP-Regulates A-type Lamins and Significantly Improves the Solubility of Progerin It is known that MB is a highly permeable molecule that can easily enter the nucleus and bind to nuclear DNA. Thus, it is possible that in addition to targeting mitochondria, MB might also enter and function in the HGPS nucleus, thereby improving the nuclear phenotypes. In an attempt to understand how MB reduced nuclear blebbing and promoted cell proliferation, amounts of lamins A and C and progerin in Mock and MB-treated HGPS fibroblasts were compared using quantitative RT-PCR (FIG. 4D) and western blotting (FIG. 4E). We observed a transcriptional upregulation and a corresponding increase in protein amounts for all three A-type lamins after MB treatment (FIG. 4D-E). Among them, the amounts of lamins A and C appeared to have a greater increase than progerin (FIG. 4D-E).

To visualize these A-type lamins in MB treated HGPS cells, confocal microscopy analysis was conducted using antibodies against lamin A/C and/or progerin (anti-lamin A/C antibody recognizes all three and anti-progerin antibody is progerin specific). Interestingly, anti-progerin antibody staining revealed a clear redistribution of progerin from the nuclear rim into the nucleoplasm in Mb treated HGPS cells. To further understand this redistribution of progerin in MB treatment, a biochemical nuclear fractionation experiment (see Methods) was carried out to separate the membrane-bounded progerin fraction (insoluble) from the nucleoplasmic fraction (soluble) in both HGPS and normal cells (FIG. 4F). Notably, in this experiment, the membrane-bounded prelamin A only presented in the insoluble fractions 9 FIG. 4F). In normal cells, 75-80% of lamin A and 55-60% of lamin C were soluble (FIGS. 4F—upper panel and 4G). FIG. 4H shows a combined analysis of soluble fractions of both lamin A and lamin C (A+C), revealing that in normal fibroblasts about 65% of A+C are soluble (FIG. 4H). Moreover, it was found that MB treatment did not cause a significant change in the solubility of lamin A or C in the normal fibroblasts (FIG. 4G-H).

In a parallel experiment, we examined the solubility of lamins A and C and progerin in HGPS fibroblasts (FIGS. 4F—lower panel and 4I). The following differences in HGPS cells were noted: first, the quantitative analysis indicated that only about 30% of progerin was soluble in the Mock-treated HGPS sample, which is much lower than either lamin A or lamin C (FIG. 4I—middle columns); second, there was a decrease in soluble fraction of lamin A from about 75% in normal cells to about 55% in HGPS sample (FIG. 4I—left columns), which is likely due to the dimerization or oligomerization of the insoluble progerin with lamin A; finally, after MB treatment, the soluble fraction of progerin was increased dramaticall from 30 to about 65%, and the soluble fractions of lamins A and C also increased by 8-10% correspondingly (FIG. 4I). The combined analysis of all soluble fractions of A-type lamins (A+P+C) revealed that MB treatment pumped the solubility of A-type lamins from 50 to near 64% (FIG. 4J), which became comparable with the percentage in normal cells (about 67%, FIG. 4H). Together, these experiments demonstrate that MB treatment promotes the expression of A-type lamins, especially lamin A and C. Additionally, MB treatment released progerin from the nuclear membrane, and significantly increased the solubility of the progerin.

EXAMPLE 6

Figure 4:
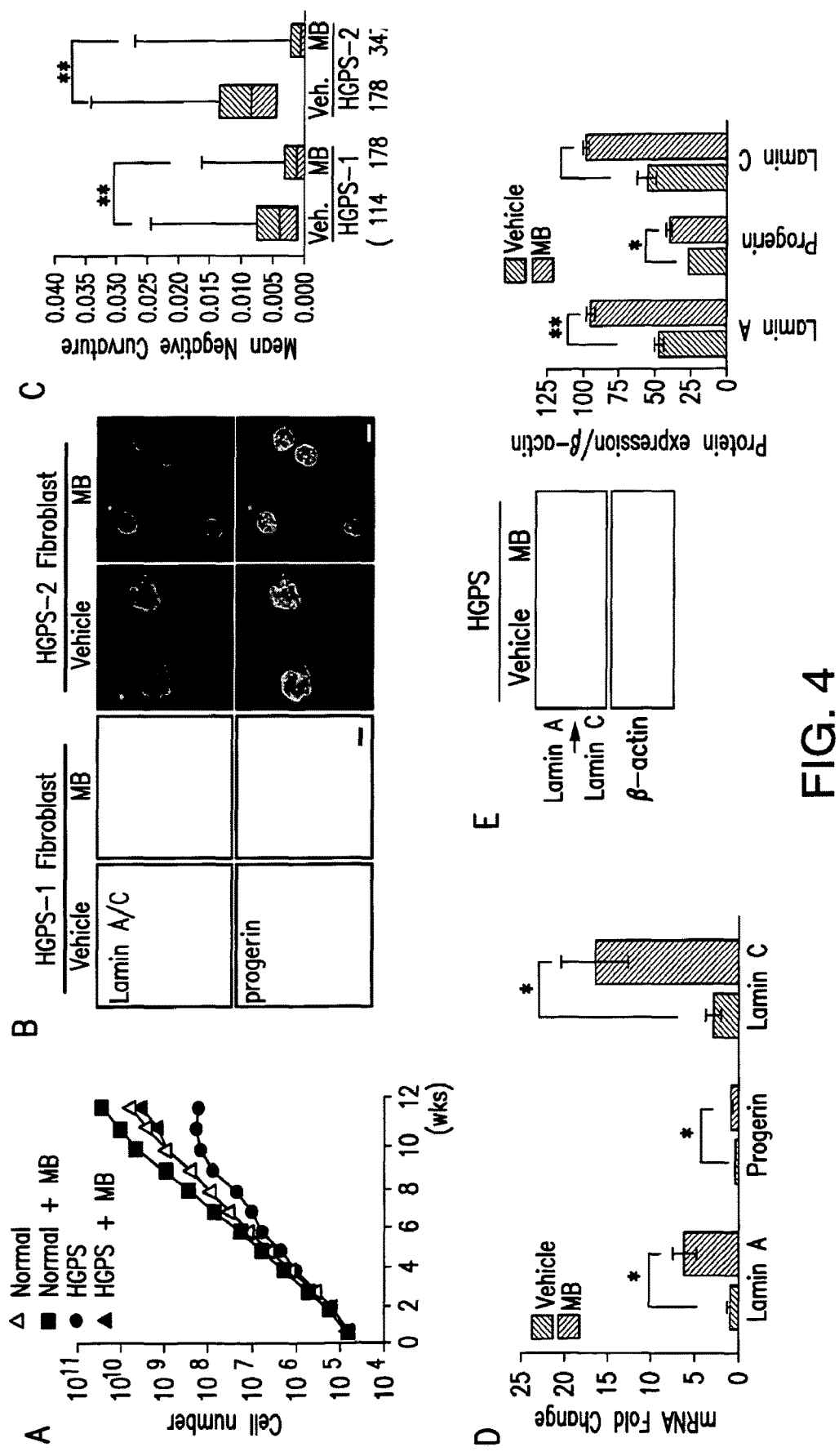
FIG. 4(A)-(I): MB Improves HGPS Nuclear Morphology and Solubilizes Progerin
- (A) Growth curves of normal and HGPS fibroblasts treated with vehicle or methylene blue (MB) at 100 nM for 12 weeks. The treatment started at the passage 14 for all cell lines, and ended at passage 20 when the HGPS cells in Mock treatment reached senescence. See line plots (1)-(4).
- (B) Representative immunofluorescence images of HGPS-1 and HGPS-2 fibroblasts treated with vehicle or MB 100 nM for 8 weeks. Red: anti-lamin A/C antibody, Green: anti-progerin antibody.
- (C) Quantification of mean negative curvature (MNC) in HGPS-1 and HGPS-2 fibroblasts treated with vehicle or MB at 100 nm for 8 weeks. Over 100 nuclei from each group were randomly selected, and their boundaries were quantitatively analyzed using the known nuclear morphology analysis software reported by Driscoll. The number of nuclei in each group is indicated in the parentheses underneath each cell type ($**p<0.01$).
- (D) Quantitative RT-PCR analysis of lamin A, progerin and lamin C mRNA levels in HGPS fibroblasts treated with vehicle or MB at 100 nM for 6 weeks ($*p<0.05$).
- (E) Left: Western blotting analysis with anti-lamin A/C and anti-β-actin antibodies in HGPS fibroblasts treated with vehicle or MB 100 nM for 6 weeks. Two technical replicates per sample were shown. Right: Quantification of relative protein amounts of lamin A, progerin and lamin C.
- (F) Nuclear fractionation and western blotting showing the input, soluble and insoluble fractions of lamin A, progerin and lamin C. Normal and HGPS fibroblasts were in treatment with vehicle or MB 100 nM for 6 weeks.
- (G) Percentages of soluble (Green) and insoluble (Orange) fractions of lamin A (including prelamin A) and lamin C in normal cells. Data for each protein were collected based on the band intensities.
Figure 4:
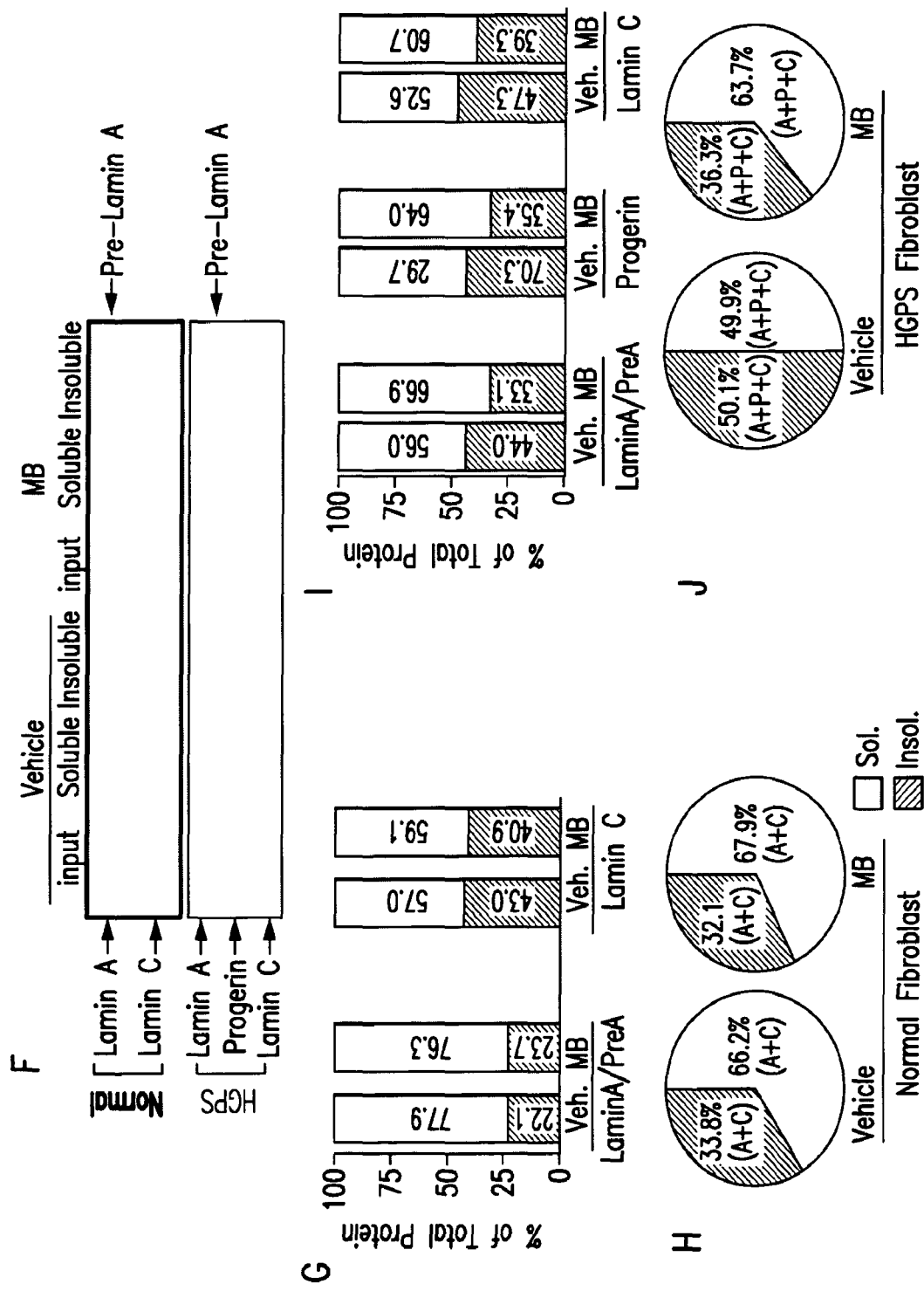
Figure 5:
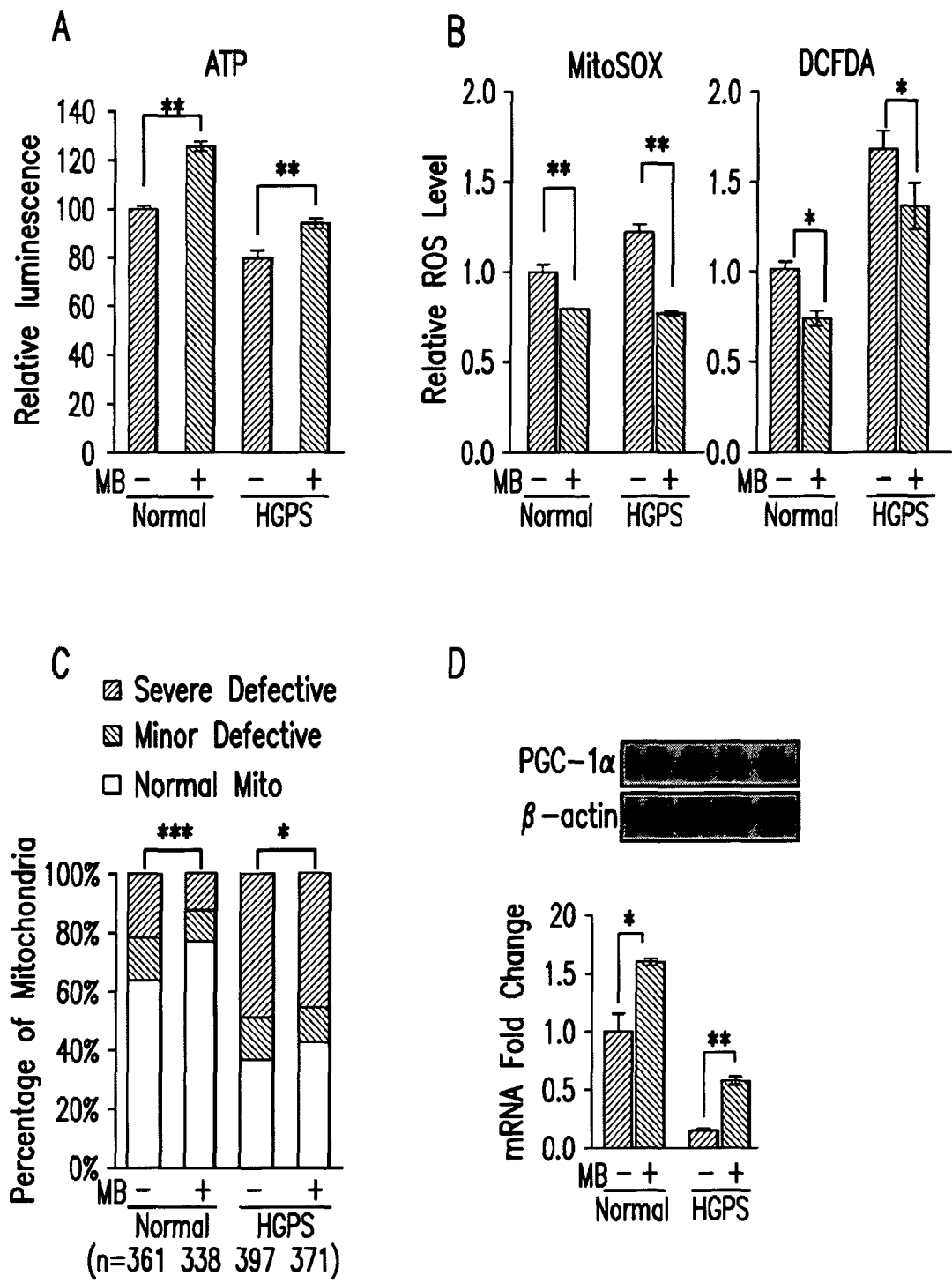
Figure 5:
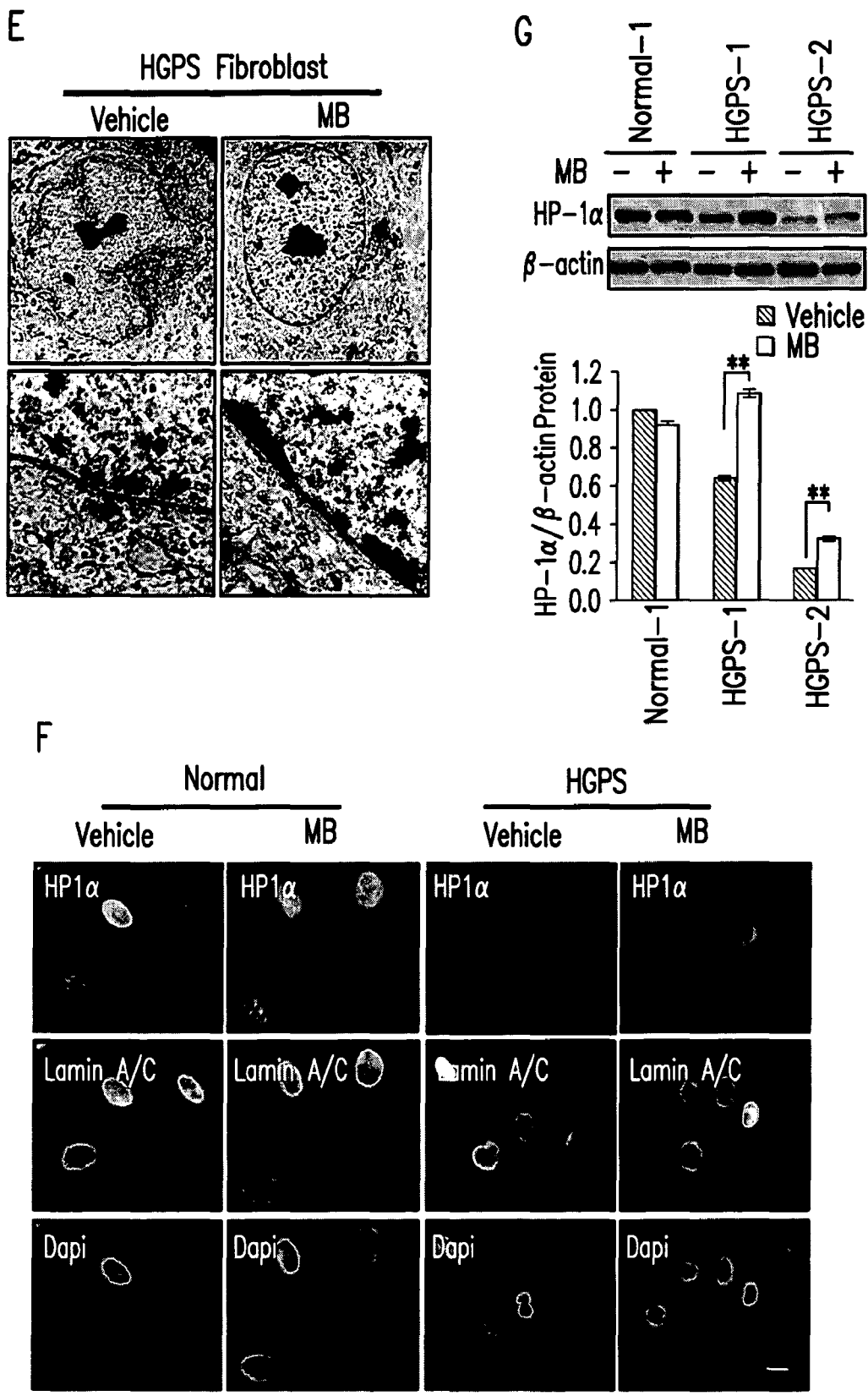

MB Reduces ROS, Improves Overall Mitochondrial Health and Stimulates PGC-1α Expression To evaluate the effects of MB on mitochondria, ATP levels, mitochondrial superoxide (MitoSOX) and overall intracellular ROS (DCFDA) in Mock or MB-treated cells. Consistent with MB's well-documented antioxidant property, Significant improvements in ATP production (FIG. 5A) and reductions in ROS levels (FIG. 5B) were found in MB-treated cells compared to Mock-treated ones. Furthermore, TEM and fluorescence microscopy studies indicated a significant reduction in the number of severely defective mitochondria after MB treatment (FIG. 5C). In addition, it was found that MB treatment stimulated the expression of PGC-1α (FIG. 5D) and thereby leading to a partial rescue of some of the PGC-1α targeted mitochondrial genes. It was concluded that treatment with MB significantly improves mitochondrial function and morphological abnormalities and stimulates PGC-1α production. Notably, in contrast to the nuclear blebbing, and progerin solubility analysis (FIG. 4) that appeared to be HGPS specific, the mitochondria in both normal and HGPS bells benefitted from MB treatment.

EXAMPLE 7

MB Rescues Perinuclear Heterochromatin Loss and Corrects Misregulated Gene Expression in HGPS Cells Based on the results from FIG. 4 and FIGS. 5A-D, it was hypothesized that While MB is a universal mitochondrial-targeting antioxidant for both normal and HGPS cells, it has a specific role in HGPS cells by dislocating progerin away from the nuclear membrane. Previous studies reported that the anchorage of progerin to the nuclear membrane caused a loss of perinuclear heterochromatin in HGPS Cells. Using TEM technology, this progerin-directed nuclear phenotype was examined in Mock and MB-treated cells, and a readily apparent restoration of perinuclear heterochromatin organization was observed after MB treatment (FIG. 5E). The rescue of heterochromatin loss by MB was further verified by immunostaining and western blotting using an antibody against heterochromatin protein 1alpha (HP1α). As a heterochromatic marker, HP1α was shown to be significantly downregulated in HGPS nuclei. These experiments demonstrated that MB treatment led to an increase in nuclear HP1α staining (FIG. 5F) and an upregulation of HP1α protein level in HGPS cells (FIG. 5G), clearly supporting the conclusions described herein.

Figure 1:
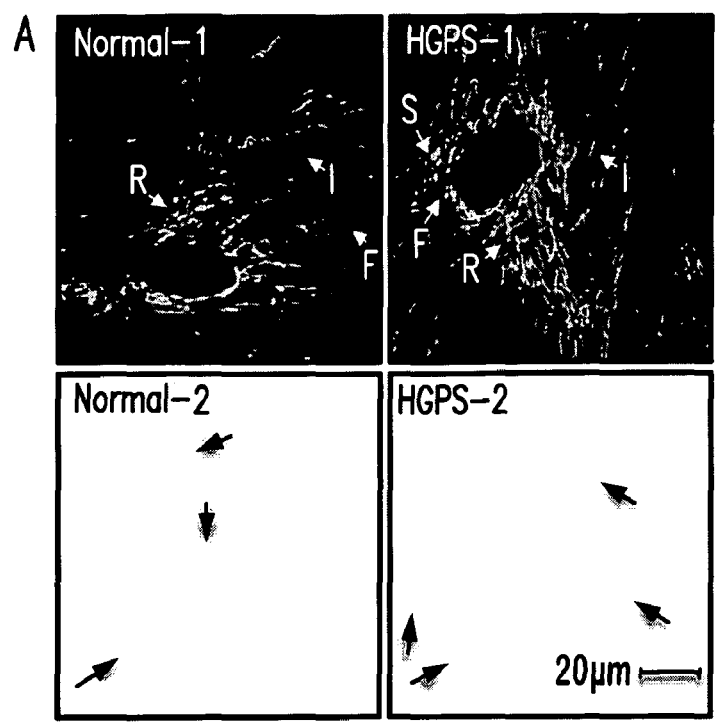
FIG. 1A-D illustrate morphological abnormalities of mitochondria in HGPS fibroblasts.
- (A) Representative fluorescence images of the mitochondria stained by MitoTracker Green FM in two normal fibroblast lines and two HGPS fibroblast lines. R: reticular mitochondria; I: intermediate mitochondria; F: fragmented mitochondria; S: swollen mitochondria.
- (B) Representative fluorescence images of normal fibroblasts transduced with lentivirus expressing either GFP-Lamin A (GFP-LA) or GFP-Progerin (GFP-Pr). The mitochondria were stained by MitoTracker Red CMXRos.
- (C) Representative transmission electron micrographs (TEM) of mitochondria taken from either normal-1 (control) or HGPS-1 (G608G) fibroblasts showing various morphological alterations raging from "Normal Mitochondria" (a-b), "Minor Defective Mitochondria" (c-d) to "Severe Defective Mitochondria" (e-h). These three general categories for phenotype grading were classified based on the intactness of membrane (outer, inner and cristae), matrix integrity and overall organelle shape: mitochondria with intact membrane and matrix were considered as "Normal Mitochondria" (a-b); mitochondria with broken membrane or or with small vacuole areas in matrix (less than 20% of the total area) were considered as "Minor Defective Mitochondria" (c-d); and mitochondria that were either morphologically abnormal (swollen or budding), or with large vacuole areas (over 20% of the total area) were defined as "Severe Defective Mitochondria" (e-h). Over 300 mitochondria in either normal-1 or HGPS-1 fibroblasts were blindly scored according to these criteria. Arrows pointed to abnormalities.
- (D) Percentages of mitochondria with different types of abnormalities in normal-1 or HGPS-1 fibroblasts. The number of mitochondria that were blindly scored in each group is indicated in the parentheses ($***p<0.001$ by Chi-square test).
Figure 1:
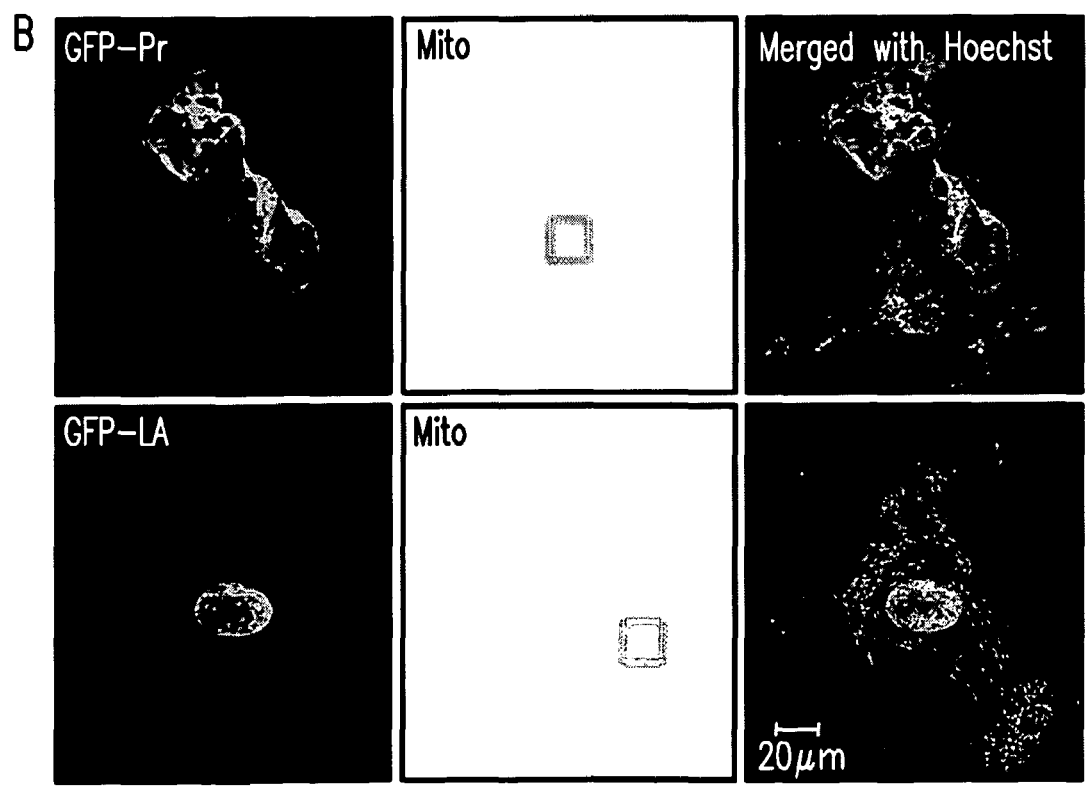
Figure 1:
Figure 1:
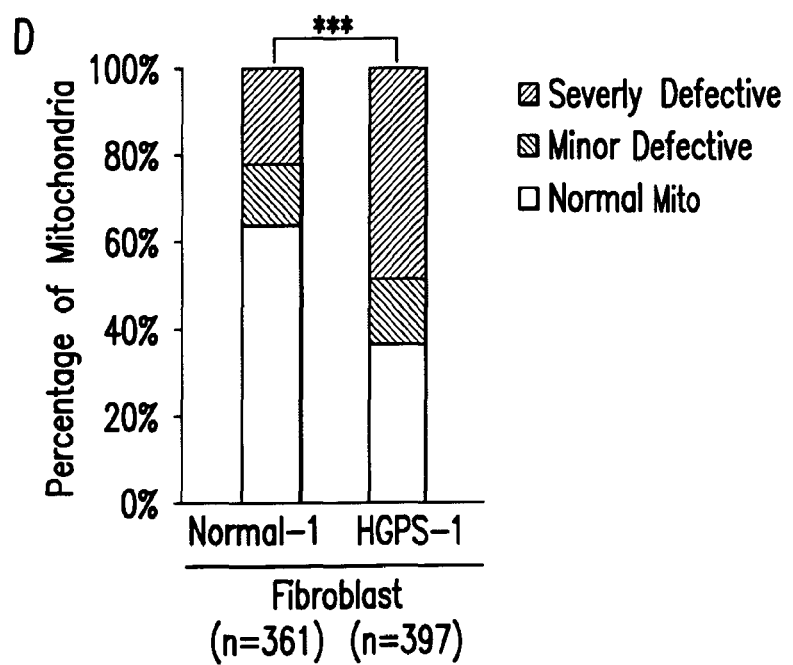

Chromatin re-organization after MB treatment may induce gene expression changes. To examine the effects of MB on gene expression, RNA-seq was conducted in Mock and MB treated normal and HGPS cells, and gene expression differential analysis was performed using Tophat and Cufflinks suite of tools (see Methods). The RNA-seq data was obtained from two biological replicates; each included four groups of samples (Normal+Vehicle; Normal+MB; HGPS+Vehicle; and HGPS+MB). Pairwise comparisons were conducted (FIG. 6A-B). Consistent with previous studies, there are more than 20% differentially expressed genes (up/down: 7.79%/14.18%) in HGPS cells vs. normal fibroblasts (FIG. 6A-1). It was found that these differentially expressed genes overlapped significantly with previous microarray and RNA-seq studies. When Normal+Vehicle vs. Normal+Mb was compared, only a few genes showed significant expression changes (up/down: 0.19%/0.14%, FIG. 6A-2), indicating that MB does not interfere with normal gene expression. However, in comparing HGPS+Vehicle vs. HGPS+MB, a significant increase in genes affected by MB in the HGPS samples was noted (up/down: 1.52%/0.45%, FIG. 6A-3), which suggests that the effect of MB on gene expression is relatively specific to HGPS cells, which might be related to the prior observation that MB specifically improved the solubility of lamin A/ C in normal control. Significantly, after one month of MB treatment, when comparing Normal+Vehicle vs. HGPS+MB, it was found that the number of differentially expressed genes in MB-treated HGPS cells was reduced to 1674 (FIG. 6A-4). Collectively, the results demonstrated that MB specifically plays a role in the HGPS nucleus, restoring the perinuclear heterochromatin and correcting misregulated gene expression.

EXAMPLE 8

2-Dimensional

1. Cell Growth and Proliferation Assay:

The normal human skin fibroblast line was cultured in MEM (Life Sciences) supplemented with 15% FBS (Gemini Bio-Products) and 2 mM L-glutamine (Life Sciences) at 37° C. with 5% $CO_2$. Methylene blue was dissolved in PBS and added to the growth medium at a final concentration of 10 or 100 nM. N-acetyl-L-cysteine (NAC), MitoQ or Mito-Tempo were added to the growth medium at the indicated concentration. The medium was changed twice a week and the cultures were passaged 1:3 at 95% confluency into fresh medium. The cell numbers in each treatment were counted weekly. See results in FIG. 9.

2. Cell Stress Assay (MitoSOX)

To measure mitochondrial superoxide, MB or other antioxidant treated skin fibroblast cells cultured on 60-mm dishes were incubated with fresh complete medium containing 5 µM MitoSOXRed (Life Technologies) at 37° C. After 30 minutes, stained cells were harvested by trypsin digestion and rinsed twice with PBS. Single cell suspensions in 400 µl PBS were prepared for FACS analysis (FACS Canto II; BD). MitoSOX Red was excited by laser at 488 nm, and the data was collected at 582±21 nm. See results in FIG. 10.

3. Cell Viability After $H_2O_2$ Insults

MB or other antioxidant treated skin fibroblast cells were incubated with PBS containing $H_2O_2$ at 1 mM for 60 minutes. The cells were then washed three times using PBS and subjected to a cellular stress assay (as described above in 2). See the results obtained in FIG. 11.

EXAMPLE 9

3-Dimensional

1. MTT Tissue Viability Tests

Skin tissues were treated with various concentration of MB for 60 minutes, and MTT assay was performed on the treated tissue. No skin irritation was observed with MB exposure on skin tissue. See results obtained in FIG. 12.

2. Skin Hydration Tests

Skin tissues were treated with MB for 2 weeks, then skin hydration was detected by using DPM9003 with 4 mm probe. It was observed that MB did not increase skin hydration. See the results obtained in FIG. 13. The noted small variations appear to have been due to pressure and leakage of medium.

3. ECM Expression:

EFT-412 tissues were treated with MB for 2 weeks. Total RNA from each treated tissue was extracted with Trizol (Life Sciences) and purified using the RNeasy Mini Kit (Qiagen) according to the manufacturer's instructions. The RNA yield was determined using the NanoDrop 2000 spectrophotometer. 1 μg of total RNA was converted to cDNA using iScript Select cDNA Synthesis Kit (Bio Rad). Quantitative RT-PCR was performed in triplicate using SYBR Green Supermix (Bio Rad) on CFX96 real-time system (C1000 Thermal Cycler; Bio Rad). Using RCP arrays for ECM remodeling genes. See results obtained in FIG. 14.

4. Histological Analysis:

H&E staining on the MB treated skin tissues. It was observed that MB increased dermis thickness. See the results obtained in FIG. 15.

EXAMPLE 10

The Synergistic Effects of MB and Rapamycin on Skin Cells

1. The Synergistic effects of MB and Rapamycin on Promoting Skin Cell Proliferation.

For varying amounts of each of MB and Rapamycin (applied together) versus a control, the effects of each on skin cell proliferation was observed. See the results obtained in FIG. 16.

2. The Synergistic Effects of MB and Rapamycin on Reducing Cellular Stress

For varying amounts of each of MB and Rapamycin (applied together) versus a control, the effects of each on reducing cellular stress was observed. See the results obtained in FIG. 17.

The conclusions reached from the 3D tests were; 1) MB does not irritate skin, 2) MB has little or no effect on normal gene expression, 3) MB increase dermis thickness, 4) MB and Rapamycin promote skin cell proliferation, and 5) MB and Rapamycin reduce cellular stress.

The materials and methods used in the examples above are described below.

Materials and Methods

Cell Culture and Drug Treatment

The normal and HGPS human skin fibroblast lines were obtained from Progeria Research Foundation (PRF). Both progeria cell lines carry the classic C1824T mutation. All fibroblast cell lines were cultured in MEM (Life Sciences) supplemented with 15% FBS (Gemini Bio-Products) and 2 mM L-glutamine (Life Sciences) at 370C with 5% $CO_2$. Methylene blue (MB, Acros Organics) was dissolved in PBS and added to the growth medium at a final concentration of 10 or 100 nM. N-Acetyl-L-cysteine (NAC, Acros Organics) was dissolved in PBS and added to the growth medium at a final concentration of 1mM. Fresh medium was provided twice a week and the cultures were passaged 1:3 at 95% confluency.

Generation of Lentiviruses

Lentiviral constructs expressing GFP-laminA or GFP-progerin or PGC-1α-his (Addgene #10974) were made by the known procedure of Kageyama et al. In brief, the GFP-laminA, GFP-progerin or PGC-1α-his was subcloned into the pHR-SIN-CSGW vector using BamHI and NotI cloning sites. After sequencing verification, these lentiviral constructs were cotransfected into HEK293T cells with two packaging vectors, pHR-CMV-8.2ΔR, and pCMV-VSVG using Fugene 6 (Promega, E2692). Two days after transfection, the culture supernatant containing viruses were clarified by filtration through 0.45 μm filters and stored at −80° C.

Transmission Electron Microscopy (TEM)

Passage-matched normal or HGPS skin fibroblasts were grown on 35-mm glass bottom dish until 80% confluence. Cells were prepared for transmission electron microscopic analysis following the protocol of McCord et al. Briefly, cells were fixed with 2.5% glutaraldehyde in 0.1 M sodium cacodylate (pH 7.4) for one hour at room temperature. Specimens were washed three times with 0.1 M sodium cacodylate and post-fixed for one hour with 1% osmium tetroxide in 0.1 M sodium cacodylate at room temperature. After washing three times with distilled water, specimens were incubated with 2% aqueous uranyl acetate at room temperature. The specimens were dehydrated in ethanol gradients: 35% for 10min, 50% for 10min, 70% for 10min, for 95% for 10 min, and 100% for 3×5 min. The infiltration was performed in EtOH: EPON resin mixture at various ratio from 1:1, 1:2, 1:3 or complete EPON for one hour each ratio. The specimens were finally embedded in complete EPON at 60° C. over night. A small piece of resin (2 mm×2 mm) was cut to get ultra-thin sections (70 nm) and the post-staining was performed in Uranyl Acetate, 2% aqueous for 5 min and lead citrate, 0.2-0.4% aqueous for 1.5 min. Observation and micrographs were made with Zeiss EM10 CA. Mitochondrial morphological quantification was conducted blindly by a trained TEM expert. Two observers scored over 360 mitochondria from 10 randomly selected cells in each group blindly. Three general categories for phenotype grading were classified based on the intactness of membrane (outer, inner and cristae), matrix integrity and overall organelle shape: mitochondria with intact membrane and matrix are considered as "normal" (a-b); mitochondria with broken membrane or with small vacuole areas in matrix (less than 20% of the total area) are considered as "minor defects"(c-d) and mitochondria that are either morphologically abnormal (swollen or budding), or with vacuole areas (over 20% of the total area) are defined as "Severe Defects" (e-h). Over 300 mitochondria in either normal or HGPS lines were blindly scored according to these criteria.

Mitochondrial Live Imaging

Skin fibroblasts were grown on 35-mm glass bottom dish until 60% confluence. For G1 phase synchronization, fibroblast cells were synchronized by serum starvation for 24 hours. Mitochondria were stained with 50 nM of MitoTracker Green FM (M7514; Life Science) or 100 nM of MitoTracker Red CMXRos (M7512; Life Science) for 20 min then maintained in fresh culture medium at 37° C., and 5% $CO_2$ during imaging. The Mitochondrial live images were acquired by Velocity Suite (PerkinElmer) using a spinning disk confocal microscopy system (UltraVIEW VoX; PerkinElmer) attached to an inverted microscope (Eclipse Ti; Nikon) with a 40×1.4 N.A. objective and equipped with a C9100-50 camera (Hamamatsu). Images were acquired at an interval of 10 s for 5 min and data analysis was performed using Velocity (version 6.3; PerkinElmer).

Reactive Oxygen Species (ROS) Assays by Flow Cytometry

To measure mitochondrial superoxide, cells grown on 60-mm dishes were incubated with fresh complete medium containing 5 μM MitoSOX Red (Life Technologies, M36008) at 37° C. After 30 minutes, stained cells were harvested by trypsin digestion and rinsed twice with PBS. Single cell suspensions in 400 μl PBS were prepared for FACS analysis (FACS Canto II; BD). MitoSOX Red was excited by a laser at 488 nm, and the data was collected at 582±21 nm. For cellular ROS measurement, cells grown on 60-mm dishes were dissociated by trypsin digestion, rinsed with PBS, and then incubated in 1× dilution buffer containing 12.5 μM DCFDA (Abcam, ab113851) at 37° C. After 30 minutes, the DCFDA was excited by laser at 495 nm, and the data was collected at 530±15 nm. Mitochondrial membrane potential (MMP, Life Technologies, M34152) and Annexin V-positive apoptotic cells (BD Pharmingen, 556547) were measured according to manufacturer's protocol. Flow cytometry was performed by FACS CantoII (BD) and the data were analyzed by FlowJo Software.

RNA Extraction, cDNA Synthesis, Quantitative RT-PCR

Total RNA from various cell lines was extracted with Trizol (Life Sciences) and purified using the RNeasy Mini Kit (Qiagen) according to the manufacturer's instructions. The RNA yield was determined using the NanoDrop 2000 spectrophotometer. Total RNA 1 μg was converted to cDNA using iScript Select cDNA Synthesis Kit (Bio-Rad). Quantitative RT-PCR was performed in triplicate using SYBR Green Supermix (Bio-Rad) on CFX96 real-time system (C1000 Thermal Cycler; Bio-Rad). All primers used in this study are listed as in Supplemental Table 1 at the end of this specification where both sense and antisense primer sequences are listed for quantitative PCR (Human).

For RNA sequencing experiments, the cell pellets of Normal or HGPS fibroblasts were collected from two individually cultured cells treated with vehicle or 100 nM MB from P15 or P16 to P20. Total RNA was extracted with Trizol (Life Sciences), followed by RNA precipitation with isopropanol, then purified using the RNeasy Mini Kit (Qiagen). The RNA quality was checked using Agilent 2100 Bioanalyzer showing good RIN numbers (8.90–9.70) in all eight samples. The RNA-seq sample preparation and sequencing were conducted according to the Illumina Truseq RNA sample preparation V2 guide by the IBBR Sequencing Core Facility at the University of Maryland. RNA-seq mapping and gene expression differential analysis was performed using Tophat and Cufflinks suite of tools as described previously by Trapnell et al.

Immunocytochemistry

Immunostaining was carried out using the following antibodies: lamin A/C (MAB3211; Millipore), progerin (Cao, et al.), PGC-1α (Thermo Scientific), DAPI (Vector Laboratories) was used to counterstain cell nuclei. Images were acquired with either Zeiss A×10 microscope equipped with a SPOT PURSUIT camera or Zeiss LSM 710 confocal microscope. Fluorescence intensity was analyzed with Image J or the known custom program of Driscoll et al.

Western Blotting

Whole cell lysates for immunoblotting were prepared by dissolved cells in Laemmli Sample Buffer containing 5% 2-mercaptoethanol (Bio-Rad). Antibodies used in this study included: PCG-1α (KP9803, Calbiochem), lamin A/C (sc-6215; Santa Cruz), progerin (Cao, et al.), HP-1α (#2616, Cell Signaling), p16 (sc-468, Santa Cruz) and β-actin (A3854, Sigma-Aldrich).

Senescence Associated β-Galactosidase Activity Assay

SA-β-gal activity assay was performed according to the manufacturer's protocol (#9860; Cell Signaling). Briefly, fibroblasts cells grown on six-well plate were fixed in 1× fixative solution containing 2% formaldehyde and 2% glutaraldehyde for 10 minutes, and then stained overnight at 37° C. with the (3-galactosidase staining solution at pH 6.0 for 15 hours. Images were acquired by Zeiss AX10 microscope with a SPOT PURSUIT camera.

Fractionation of Fibroblast Nuclei

Fibroblast cells grown on a 100-mm dish were harvested with 0.05% trypsin-EDTA when they reached 70% confluence and rinsed with ice-cold PBS twice. Nuclei were separated from cytoplasm following the manual of NE-PER Nuclear And Cytoplasmic Extraction Reagents (#78835, Thermo Scientific). After centrifuging, the cytoplasm supernatant was removed. The pellets containing nuclei were re-suspended well in lysis buffer (50 mM Tris-HCl pH 7.4, 150 mM Nacl, 1% Triton X-100, 0.1% Deoxycholate, Complete Mini protease inhibitor cocktail tablet) and subjected to slight sonification at 20% amplitude for 30 sec. (FB120, Fisher Scientific). The whole nuclei lysate was further centrifuged at 16,000 g for 5 min. The supernatant was saved as the insoluble fraction of the nuclei. Both fractions of nuclei were prepared for western blot assay by adding Laemmli Sample Buffer (Bio-Rad). A one-fifth portion of either soluble or insoluble fraction sample was loaded onto 10% SDS-PAGE gel, and then proceeded for western blot analysis. Images were taken with ChemiDoc™ Touch Imaging System (Bio-Rad), and band intensity analysis was carried out with Image Lab software 5.2.1 (Bio-Rad).

ATP Assay

Intracellular ATP content was measured by using luminescence ATP detection System (ATPlite, PerkinElmer). Briefly, fibroblast cells were harvested with 0.05% trypsin-EDTA and counted. The same number of 2,500 cells from each fibroblast sample was seeded onto a 96-well black plate (triplicate). After the cells had been lysed with the lysis buffer for five minutes, the substrate solution was added and mixed for another five minutes to conduct the reaction for light generation. After dark adaption for 10 minutes, the luminescence intensity of each well was acquired at luminescence mode with SoftMax Pro software connecting to SpectraMax M5 Microplate Reader.

Quantification of Mitochondria DNA (mtDNA)

The whole DNA, including genomic and mitochondrial DNA from fibroblasts was extracted with UltraPure™ Phenol: Chloroform:Isoamyl Alcohol (25:24:1) (15593-031), ThermoFisher Scientific). Instead of proceeding to the column isolation, DNA was precipitated with ethanol to avoid mtDNA loss. DNA concentration was measured using a NanoDrop 2000 spectrophotometer (Thermo Scientific). The total amount of 100 ng of DNA was added into a 15 μl qPCR reaction system with either mtDNA primers or s18 RNA primers (see Supplemental Table 1). The level of mtDNA was calculated using the delta Ct ($\Delta$Ct) of average Ct of mtDNA and nDNA ($\Delta$Ct=CtmtDNA−CtnDNA) in the same well as an exponent of 2 (2$\Delta$Ct).

Statistical Analysis

Results are presented as mean±SD (standard deviation). Data were analyzed using 2-tailed Student's t test, and a p value less than 0.05 was considered significant. A chi-square test was conducted to compare the distribution difference of mitochondria with various ultrastructural abnormalities in normal and HGPS fibroblasts.

Rapamycin, itself, may be prepared as described in U.S. Pat. No. 3,929,992, and its many substituted versions as described in the U.S. patents noted in the Term Definition section. All of these patents, including U.S. Pat. No. 3,929, 992, are incorporated herein in the entirety.

The compositions of the present invention, as noted above, may contain MB or MB and rapamycin as active ingredients, or may contain a single MB derivative or MB and one or more MB derivatives. These compositions may also contain one or more substituted rapamycin compounds or one or more substituted rapamycin compounds with MB or MB and one or more MB derivatives.

The following examples of pharmaceutical formulations are provided solely for purposes of illustration and are not intended to be limitative.

All weight percentages given below are based on total weight of the composition. in the examples below, any of the methylene blue derivatives or rapamycin derivatives may be used in addition to methylene blue or rapamycin.

EXAMPLE 11

A topical formulation:
1% by weight of rapamycin.
100 micrograms of methylene blue.
petrolatum as a carrier. Petrolatum is a semi-solid mixture of hydrocarbons with carbon numbers mainly higher than 25. See U.S. Pat. No. 127,568, which is incorporated herein by reference in the entirety.

EXAMPLE 12

A topical formulation in the form of a lotion:
Per 20 ml of lotion:
100 micrograms of methylene blue
QS with water and emollient to form a thick lotion.

EXAMPLE 13

An oral formulation as a dispersion:
1 mg of rapamycin
0.5 mg of poloxamer 188
98 mg of sucrose
0.5 mg of povidone
1 mg of microcrystalline cellulose
50 mg of water.

EXAMPLE 14

A soap is formulated using the formulation of U.S. Pat. No. 5,547,602A, which patent is incorporated herein in the entirety, but with methylene blue and/or rapamycin added thereto.

Although the present invention specifically contemplates alleviation of age-related symptoms of humans, alleviation of age-related symptoms of mammals generally is also contemplated for veterinary use. Mammals such as cows, sheep, goats, dogs, cats and horses may be mentioned. Mice and rats may also be mentioned for testing purposes.

Having described the present invention, it will be apparent to those skilled in the art that non-inventive changes and modifications may be made to the above-described embodiments without departing from the spirit and the scope of the claimed invention.

What is claimed is:

1. A topical pharmaceutical composition in a form of a cream, lotion or gel for alleviating age-related symptoms in human skin which comprises:
   a) a low concentration of methylene blue sufficient to alleviate said age-related symptoms; said concentration of said methylene blue being sufficient to prolong cellular viability in said human skin and in a concentration of no more than 1 micromolar (1 µM) in said composition, and
   b) a pharmaceutically-acceptable excipient in an amount suitable for topical administration of said composition to said human skin.

2. The pharmaceutical composition of claim 1, which is in a form of a cosmetic or dermatological composition.

3. The pharmaceutical composition of claim 1, which is in a form of a lotion.

4. The pharmaceutical composition of claim 1, which is in a form of a gel.

5. The pharmaceutical composition of claim 1, which is in a form of a cosmetic.

6. The pharmaceutical composition of claim 1, wherein said pharmaceutically-acceptable excipient comprise solvent, lubricants, emollients, emulsifiers, moisturizers, thickening wax, softeners, fragrances, preservatives or coloring agents.

7. The pharmaceutical composition of claim 1, which is in a form of unit dosages.

8. The pharmaceutical composition of claim 1, wherein said methylene blue is present in said composition in a concentration of at least 0.02 micromolar.

9. The pharmaceutical composition of claim 1, wherein said methylene blue is present in said composition in concentration of about 0.5 micromolar.

10. The pharmaceutical composition of claim 1, which is in a form of a cream.

11. The pharmaceutical composition of claim 10, wherein said cream is a moisturizing cream.

12. The pharmaceutical composition of claim 3, wherein said lotion is a moisturizing lotion.

13. The pharmaceutical composition of claim 1, wherein said alleviating age-related symptoms in human skin comprises promotion of human skin cell proliferation and viability, and reduction of reactive oxygen species in cells of human skin.

* * * * *